United States Patent

Cunningham et al.

[11] Patent Number: 6,045,974
[45] Date of Patent: Apr. 4, 2000

[54] BORATE PHOTOINITIATORS FROM MONOBORANES

[75] Inventors: Allan Francis Cunningham, Marly, Switzerland; Martin Kunz, Efringen-Kirchen, Germany; Hisatoshi Kura, Hyogo, Japan

[73] Assignee: Ciba Specialty Chemicals Corporation, Tarrytown, N.Y.

[21] Appl. No.: 09/247,147

[22] Filed: Feb. 9, 1999

Related U.S. Application Data

[62] Division of application No. 08/755,771, Nov. 21, 1996, Pat. No. 5,932,393.

[30] Foreign Application Priority Data

Nov. 24, 1995 [CH] Switzerland .............................. 3344/95

[51] Int. Cl.⁷ .............................. G03C 1/725; C08F 2/46; C08F 4/52
[52] U.S. Cl. .......................... 430/281.1; 522/6; 522/182; 526/196
[58] Field of Search .......................... 526/196; 522/182; 430/281.1

[56] References Cited

U.S. PATENT DOCUMENTS

| | | | |
|---|---|---|---|
| 3,567,453 | 3/1971 | Borden | 96/91 |
| 4,772,530 | 9/1988 | Gottschalk et al. | 430/138 |
| 4,772,541 | 9/1988 | Gottschalk et al. | 430/339 |
| 4,954,414 | 9/1990 | Adair et al. | 430/138 |
| 4,971,891 | 11/1990 | Kawamura et al. | 430/278 |
| 5,055,372 | 10/1991 | Shanklin et al. | 430/138 |
| 5,143,818 | 9/1992 | Weed et al. | 430/281 |
| 5,147,758 | 9/1992 | Smothers et al. | 430/281 |
| 5,151,520 | 9/1992 | Gottschalk et al. | 548/110 |
| 5,346,801 | 9/1994 | Watanabe et al. | 430/253 |
| 5,475,119 | 12/1995 | Baur et al. | 548/570 |
| 5,496,903 | 3/1996 | Watanabe et al. | 526/204 |
| 5,500,453 | 3/1996 | Toba et al. | 522/25 |
| 5,563,016 | 10/1996 | Baur et al. | 430/110 |
| 5,817,376 | 10/1998 | Everaerts et al. | 427/483 |
| 5,866,631 | 2/1999 | Nakagawa et al. | 523/118 |

FOREIGN PATENT DOCUMENTS

| | | |
|---|---|---|
| 0548826 | 6/1993 | European Pat. Off. |
| 0555058 | 8/1993 | European Pat. Off. |
| 0609452 | 8/1994 | European Pat. Off. |

OTHER PUBLICATIONS

"Review of light–sensitive tetraarylborates", Photographic Science and Engineering, vol. 16, No. 4, Jul./Aug. 1972.

Primary Examiner—Cynthia Hamilton
Assistant Examiner—Rosemary Ashton
Attorney, Agent, or Firm—Luther A. R. Hall; David R. Crichton

[57] ABSTRACT

The invention relates to photopolymerizable compositions comprising as photoinitiator a borate of the formula I or I'

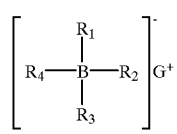

(I)

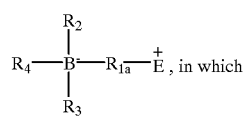

(I')

$R_1$, $R_2$ and $R_3$ are, for example and independently of one another, phenyl or another aromatic hydrocarbon, with or without any heteroatoms, which radicals are unsubstituted or are substituted, or the radicals $R_1$ and $R_2$ form bridges to produce structures of the formula II, IIa or IIb

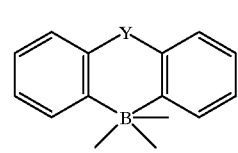 (II)

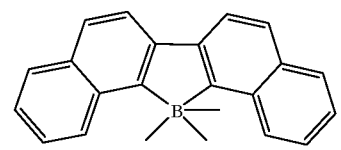

(IIa)

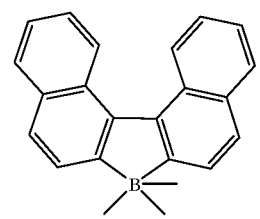

(IIb)

with the provisos that not more than two of the radicals $R_1$, $R_2$ and $R_3$ are identical and either at least two of the radicals $R_1$, $R_2$ and $R_3$ are aromatic hydrocarbon radicals or phenyl radicals which are substituted in both ortho-positions or at least one radical $R_1$, $R_2$ or $R_3$ is a sterically bulky aryl radical and the remaining radicals of $R_1$, $R_2$ and $R_3$ are aromatic hydrocarbon radicals or are phenyl radicals which are substituted in at least one ortho-position; $R_4$ is, for example, phenyl or $C_1$–$C_{20}$alkyl and G is a radical which is able to form positive ions.

8 Claims, No Drawings

BORATE PHOTOINITIATORS FROM MONOBORANES

This is a divisional of application Ser. No. 08/755,771, filed on Nov. 21, 1996 now, U.S. Pat. No. 5,932,393.

The invention relates to photopolymerizable compositions which comprise borate photoinitiators, in particular including unimolecular borate photoinitiators.

The use of borates as photoinitiators in combination with coinitiators is known in the prior art. For example, U.S. Pat. Nos. 4,772,530, 4,772,541 and 5,151,520 disclose triaryl alkyl borate anions with cationic dyes, for example cyanines, rhodamines, etc., as counterions. These compounds are employed as photoinitiators. In U.S. Pat. No. 4,954,414, cationic transition metal complexes are used together with triaryl alkyl borate anions in photopolymerizable compositions. From U.S. Pat. No. 5,055,372 it is also known to use quaternary ammonium compounds, for example tetramethylammonium, pyridinium, cetylpyridinium, etc., as cationic counterions to the triaryl alkyl borate. In this publication the borates are employed in connection with aromatic ketone initiator compounds as coinitiators in photocurable materials.

For the extensive range of applications of photointiators, there is a need in the industry for stable reactive compounds which can be used as initiators in photopolymerizable compositions.

The borate compounds described in the abovementioned publications are always used, as photoinitiators, in combination with coinitiators. In the industry it is advantageous to provide photopolymerizable compositions comprising photoinitiators which are sufficiently reactive, even without the addition of coinitiators, to initiate photopolymerization. It has surprisingly now been found that borates having defined substitution patterns possess these properties.

The invention provides a photopolymerizable composition comprising a) at least one polymerizable ethylenically unsaturated compound and b) at least one compound of the formula I or I' as unimolecular photoinitiator

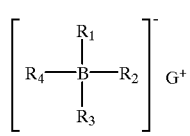

(I)

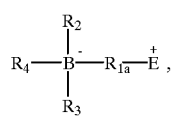

(I')

in which $R_1$, $R_2$ and $R_3$ independently of one another are phenyl or another aromatic hydrocarbon, with or without any heteroatoms, which radicals are unsubstituted or are substituted 1–5 times by unsubstituted or $OR_6$— or $R_7R_8N$— substituted $C_1$–$C_{20}$alkyl, $C_2$–$C_{20}$alkyl which is interrupted by one or more radicals O, $S(O)_p$ or $NR_5$, $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$, CN and/or

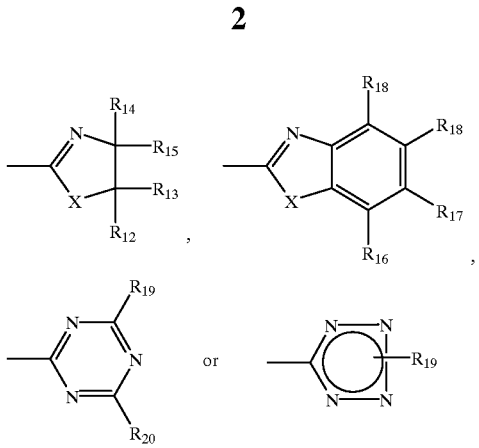

or the radicals $R_2$ and $R_3$ form bridges to produce structures of the formula II, IIa or IIb

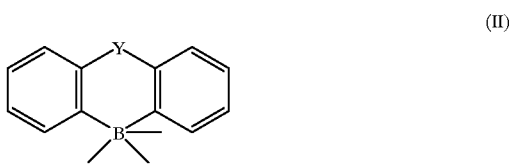

(II)

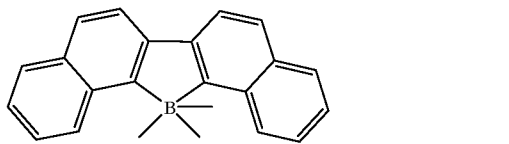

(IIa)

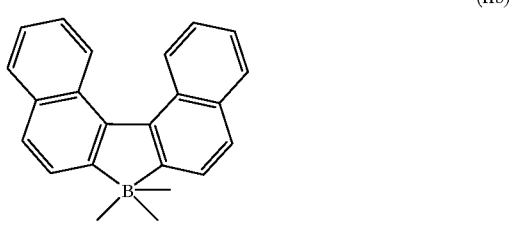

(IIb)

whose aromatic rings are unsubstituted or are substituted by $C_1$–$C_{20}$alkyl, by $C_2$–$C_{20}$alkyl which is interrupted by one or more radicals O, $S(O)_p$ or $NR_5$, or by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, halogen, $R_9R_{10}P(O)_q$ and/or $R_9R_{10}R_{11}Sn$; with the provisos that not more than two of the radicals $R_1$, $R_2$ and $R_3$ are identical and either at least two of the radicals $R_1$, $R_2$ and $R_3$ are aromatic hydrocarbon radicals or phenyl radicals which are substituted in both ortho-positions or at least one radical $R_1$, $R_2$ or $R_3$ is a sterically bulky aryl radical and the remaining radicals of $R_1$, $R_2$ and $R_3$ are aromatic hydrocarbon radicals or phenyl radicals which are substituted in at least one ortho-position;

$R_{1a}$ is a divalent aromatic hydrocarbon radical which is unsubsituted or is substituted by $C_1$–$C_6$alkyl, $OR_6$, $S(O)_pR_6$, $OS(O)_2R_6$, $NR_8R_7$, $C(O)OR_6$, $C(O)NR_8R_7$, $C(O)R_9$, $SiR_9R_{10}R_{11}$ or halogen, or $R_{1a}$ is phenyl-$C_1$–$C_6$alkylene;

$R_4$ is phenyl or another aromatic hydrocarbon radical, with or without any heteroatoms, which radicals are unsubstituted or substituted 1–5 times by unsubstituted or $OR_6$— or $R_7R_8N$-substituted $C_1$–$C_{20}$alkyl, $C_2$–$C_{20}$alkyl which is interrupted by one or more radicals O, S(O)$_p$ or NR$_5$, OR$_6$, R$_6$S(O)$_p$, R$_6$S(O)$_2$O, R$_7$R$_8$N, R$_6$OC(O), R$_7$R$_8$NC(O), R$_9$C(O), R$_9$R$_{10}$R$_{11}$Si, R$_9$R$_{10}$R$_{11}$Sn, halogen, R$_9$R$_{10}$P(O)$_q$, CN and/or

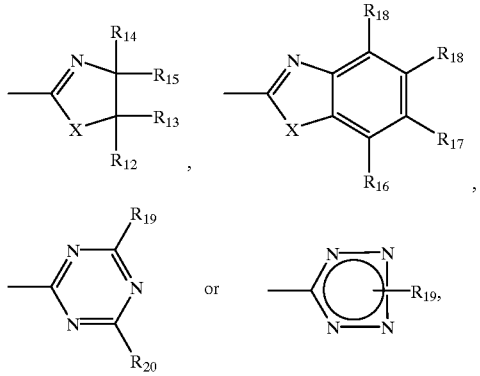

or R$_4$ is C$_1$–C$_{20}$alkyl, C$_2$–C$_{20}$alkyl which is interrupted by one or more radicals O, S(O)$_p$ or NR$_5$, or is C$_3$–C$_{12}$cycloalkyl, C$_2$–C$_8$alkenyl, phenyl-C$_1$–C$_6$alkyl or naphthyl-C$_1$–C$_3$alkyl, where the radicals C$_1$–C$_{20}$alkyl, C$_3$–C$_{12}$cycloalkyl, C$_2$–C$_8$alkenyl, phenyl-C$_1$–C$_6$alkyl or naphthyl-C$_1$–C$_3$alkyl are unsubstituted or are substituted by OR$_6$, R$_6$S(O)$_p$, R$_6$S(O)$_2$O, R$_7$R$_8$N, R$_6$OC(O), R$_7$R$_8$NC(O), R$_9$C(O), R$_9$R$_{10}$R$_{11}$Si, R$_9$R$_{10}$R$_{11}$Sn, halogen, R$_9$R$_{10}$P(O)$_q$, and/or CN;

Y is (CH$_2$)$_n$, CH=CH, C(O), NR$_5$, O, S(O)$_p$ or

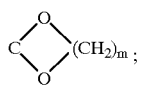

n is 0, 1 or 2;
m is 2 or 3;
p is 0, 1 or 2;
q is 0 or 1;
E is R$_{21}$R$_{22}$R$_{23}$P, R$_7$R$_{7a}$R$_8$N or R$_6$R$_{6a}$S;
R$_5$ is hydrogen, C$_1$–C$_{12}$alkyl, phenyl-C$_1$–C$_6$alkyl or phenyl, where the radicals phenyl-C$_1$–C$_6$-alkyl or phenyl are unsubstituted or are substituted 1–5 times by C$_1$–C$_6$alkyl, C$_1$–C$_{12}$alkoxy and/or halogen;
R$_6$ and R$_{6a}$ are unsubstituted or halogen-substituted C$_1$–C$_{12}$alkyl, phenyl-C$_1$–C$_6$alkyl or phenyl, where the radicals phenyl-C$_1$–C$_6$alkyl or phenyl are unsubstituted or are substituted 1–5 times by C$_1$–C$_6$alkyl, C$_1$–C$_{12}$alkoxy and/or halogen;
R$_7$, R$_{7a}$ and R$_8$ independently of one another are unsubstituted or C$_1$–C$_{12}$alkoxy-, halogen-, OH—, COOR$_6$— or CN-substituted C$_1$–C$_{12}$alkyl, C$_3$–C$_{12}$cycloalkyl, phenyl-C$_1$–C$_6$alkyl or phenyl, where the radicals phenyl-C$_1$–C$_6$alkyl or phenyl are unsubstituted or are substituted 1–5 times by C$_1$–C$_6$alkyl, C$_1$–C$_{12}$alkoxy and/or halogen, or R$_7$ and R$_8$, together with the N atom to which they are attached, form a 5- or 6-membered ring which may additionally contain O or S atoms;
R$_9$, R$_{10}$ and R$_{11}$ independently of one another are C$_1$–C$_{12}$alkyl, C$_3$–C$_{12}$cycloalkyl, phenyl-C$_1$–C$_6$alkyl or phenyl, where the radicals phenyl-C$_1$–C$_6$alkyl or phenyl are unsubstituted or are substituted 1–5 times by C$_1$–C$_6$alkyl, C$_1$–C$_{12}$alkoxy and/or halogen;
R$_{12}$, R$_{13}$, R$_{14}$ and R$_{15}$ independently of one another are hydrogen, unsubstituted or C$_1$–C$_{12}$-alkoxy-substituted C$_1$–C$_{12}$alkyl, unsubstituted or mono- to penta-C$_1$–C$_6$alkyl-, -C$_1$–C$_{12}$alkoxy- or -halogen-substituted phenyl-C$_1$–C$_6$alkyl or are unsubstituted or mono- to penta-C$_1$–C$_6$-alkyl-, -C$_1$–C$_{12}$alkoxy- or -halogen-substituted phenyl, or the radicals R$_{12}$, R$_{13}$, R$_{14}$ and R$_{15}$ together form an aromatic ring to which further aromatic rings may be fused;

R$_{16}$, R$_{17}$, R$_{18}$, R$_{18a}$, R$_{19}$ and R$_{20}$ independently of one another are hydrogen, unsubstituted or C$_1$–C$_{12}$alkoxy-, OH— or halogen-substituted C$_1$–C$_{12}$alkyl or are unsubstituted or C$_1$–C$_{12}$alkyl-, C$_1$–C$_{12}$alkoxy-, OH— or halogen-substituted phenyl;

R$_{21}$, R$_{22}$ and R$_{23}$ independently of one another are C$_1$–C$_{12}$alkyl, C$_2$–C$_{12}$alkenyl or C$_3$–C$_{12}$cycloalkyl, where the radicals C$_1$–C$_{12}$alkyl, C$_2$–C$_{12}$alkenyl and C$_3$–C$_{12}$cycloalkyl are unsubstituted or are substituted by R$_6$OCO or CN, or R$_{21}$, R$_{22}$ and R$_{23}$ are unsubstituted or mono- to penta-C$_1$–C$_6$alkyl-, -C$_1$–C$_{12}$alkoxy- or -halogen-substituted phenyl-C$_1$–C$_6$alkyl or are unsubstituted or mono- to penta-C$_1$–C$_6$alkyl-, -C$_1$–C$_{12}$alkoxy- or -halogen-substituted phenyl;

X is N, S or O; and

G is a radical which is able for form positive ions.

Even without the addition of coinitiators, the compounds of the formulae I and I' are reactive initiators for the photopolymerization of ethylenically unsaturated compounds.

Features of the compounds are that, firstly, not more than two of the radicals R$_1$, R$_2$ and R$_3$ are identical and, secondly, either at least two of the radicals R$_1$, R$_2$ and R$_3$ are aromatic hydrocarbon radicals or phenyl radicals which are substituted in <u>both</u> ortho-positions, or at least one radical R$_1$, R$_2$ or R$_3$ is a sterically bulky aryl radical and the remaining radicals of R$_1$, R$_2$ and R$_3$ are aromatic hydrocarbon radicals or phenyl radicals which are substituted in at least one ortho-position.

Aromatic hydrocarbons as may be present in the novel compounds may, for example, contain one or more, especially 1 or 2, heteroatoms. Examples of suitable heteroatoms are N, O, P and S, preferably N or O. Examples of aromatic hydrocarbon radicals are phenyl, 1- and 2-naphthyl, stilbenyl, biphenyl, o-, m-, p-terphenyl, triphenylphenyl, binaphthyl, anthracyl, phenanthryl, ferrocenyl, pyrenyl, furan-2-yl or furan-3-yl, thiophen-2-yl or thiophen-3-yl, pyddin-2-yl, pyridin-3-yl, or pyridin-4-yl, pyrimidinyl, quinolyl or isoquinolyl.

Also suitable are aromatic hydrocarbon radicals of the formula

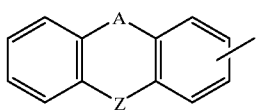

in which A and Z independently of one another are —(CH$_2$)$_n$—, —C(O)—, N, S(O)$_p$, where n and p are as defined above. Examples of these are anthracyl, fluorenyl, thianthryl, xanthyl, acridinyl, phenazinyl, phenothiazinyl, phenoxathinyl and phenoxazinyl.

Stilbenyl is
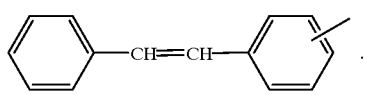
Biphenyl is
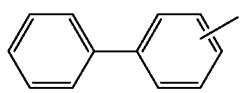
o-, m- or p-terphenyl are
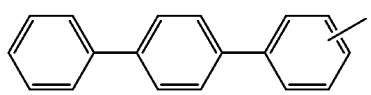
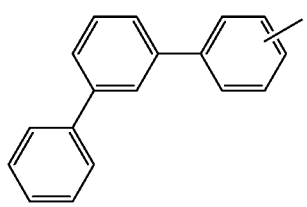
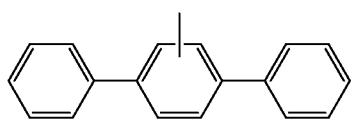
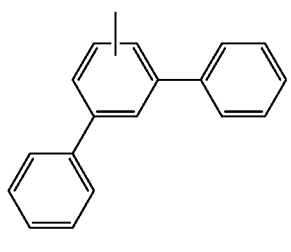
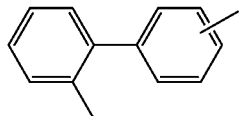
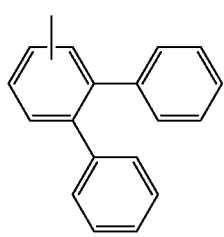
Triphenylphenyl is
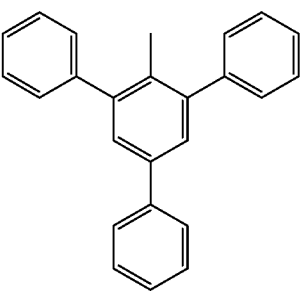
or
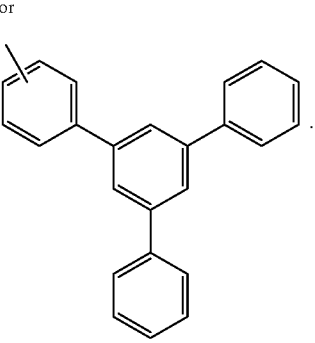
Binaphthyl is
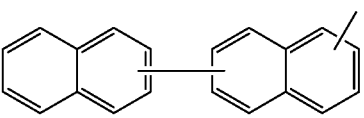
Anthracyl is
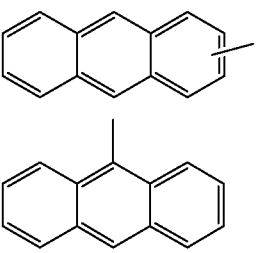
or
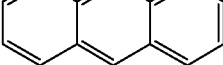
Phenanthryl is
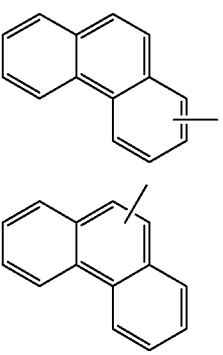
or
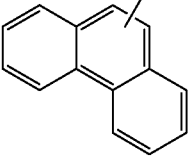

Pyrenyl is

[structure]

or

[structure]

Quinolyl is

[structure]

or

[structure]

Isoquinolinyl is

[structure]

or

[structure]

Furanyl is furan-2-yl or furan-3-yl. Thiophenyl is thiophen-2-yl or thiophen-3-yl. Pyridinyl is pyridin-2-yl, pyridin-3-yl or pyridin-4-yl.

Substituted radicals phenyl, stilbenyl, biphenyl, o-, m- and p-terphenyl, triphenylphenyl, naphthyl, binaphthyl, anthracyl, phenanthryl, pyrenyl, ferrocenyl, furanyl, thiophenyl, pyridinyl, quinolinyl or isoquinolinyl are substituted one to four times, for example one, two or three times, especially two or three times. Substituents on the phenyl ring are preferably in positions 2, 4 or 6 or in 2,6 or 2,4,6 configuration on the phenyl ring.

The term "sterically bulky aryl radical" as used in this application refers, for example, to polycycles, i.e. polycyclic aryl radicals. Examples of these are fused hydrocarbon rings without or without heteroatoms, preferably S, O or N, examples being 1- and 2-naphthyl, binaphthyl, anthracyl, phenanthryl, pyrenyl, quinolyl and isoquinolyl.

The term "sterically bulky aryl radical", however, also refers to ring sequences, i.e. aryl rings linked by single bonds. Examples of these are biphenyl, o, m- and p-terphenyl, and triphenylphenyl.

$C_1$–$C_{20}$alkyl is linear or branched and is, for example, $C_1$–$C_{12}$, $C_1$–$C_8$, $C_1$–$C_6$ or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl and eicosyl. For example, $R_4$ is $C_1$–$C_8$alkyl, especially $C_1$–$C_6$alkyl, preferably $C_1$–$C_4$akyl, for example methyl or butyl. Where $R_1$, $R_2$, $R_3$ and $R_4$ are $C_1$–$C_{20}$alkyl substituted by $R_9R_{10}R_{11}Si$, then the alkyl radical is, for example, $C_1$–$C_{12}$alkyl, especially $C_1$–$C_8$alkyl, preferably $C_1$–$C_4$alkyl. Methyl is particularly preferred.

$C_1$–$C_{12}$alkyl and $C_1$–$C_6$alkyl are likewise linear or branched and have, for example, the definitions given above up to the appropriate number of carbon atoms. $R_5$, $R_6$, $R_{6a}$, $R_7$ $R_{7a}$, $R_8$, $R_9$, $R_{10}$, $R_{11}$, $R_{12}$ and $R_{13}$ are, for example, $C_1$–$C_8$alkyl, especially $C_1$–$C_6$alkyl, preferably $C_1$–$C_4$alkyl, for example methyl or butyl. $C_1$–$C_6$alkyl substituents for phenyl-$C_1$–$C_6$alkyl or phenyl are, in particular, $C_1$–$C_4$alkyl, for example methyl or butyl.

$C_2$–$C_{20}$alkyl interrupted one or more times by —O—, —S(O)$_p$— or —NR$_5$— is, for example, interrupted 1–9 times, for example 1–7 times or 1 or 2 times by —O—, —S(O)$_p$— or —NR$_5$—. This produces structural units such as, for example, —CH$_2$—O—CH$_3$, —CH$_2$CH$_2$—O—CH$_2$CH$_3$, —[CH$_2$CH$_2$O]$_y$—CH$_3$, where y=1–9, —(CH$_2$CH$_2$O)$_7$CH$_2$CH$_3$, —CH$_2$—CH(CH$_3$)—O—CH$_2$—CH$_2$CH$_3$, —CH$_2$—CH(CH$_3$)—O—CH$_2$—CH$_3$, —CH$_2$SCH$_3$ or —CH$_2$—N(CH$_3$)$_2$.

$C_3$–$C_{12}$cycloalkyl is, for example, cyclopropyl, cyclopentyl, cyclohexyl, cyclooctyl, cyclododecyl, especially cyclopentyl and cyclohexyl, preferably cyclohexyl.

$C_2$–$C_8$alkenyl radicals can be mono- or polyunsaturated and are, for example, allyl, methallyl, 1,1-dimethylallyl, 1-butenyl, 3-butenyl, 2-butenyl, 1,3-pentadienyl, 5-hexenyl or 7-octenyl, especially allyl. $R_4$ as $C_2$–$C_8$alkenyl is, for example, $C_2$–$C_6$alkenyl, especially $C_2$–$C_4$alkenyl.

Phenyl-$C_1$–$C_6$alkyl is, for example, benzyl, phenylethyl, α-methylbenzyl, phenylpentyl, phenylhexyl or α,α-dimethylbenzyl, especially benzyl. Preference is given to phenyl-$C_1$–$C_4$alkyl, especially phenyl-$C_1$–$C_2$alkyl. Substituted phenyl-$C_1$–$C_6$alkyl is substituted one to four times, for example once, twice or three times, especially once or twice, on the phenyl ring.

Phenyl-$C_1$–$C_6$alkylene has two free bonds, of which one is on the phenylene ring and the other is in the alkylene radical:

[structure: phenyl—(C$_n$H$_{2n}$)$_x$—]

where x=1 to 6.

Substituted phenyl is substituted one to five times, for example once, twice or three times, especially once or twice, on the phenyl ring. The substituents are located, for example, in positions 2 and 6, 2 and 4 or 2, 4 and 6 of the phenyl ring, preferably in positions 2 and 6 or 2, 4 and 6.

Examples of naphthyl-$C_1$–$C_3$alkyl are naphthylmethyl, naphthylethyl, naphthylpropyl and naphthyl-1-methylethyl, especially naphthylmethyl. The alkyl unit may be in either position 1 or position 2 of the naphthyl ring system. Substituted naphthyl-$C_1$–$C_3$alkyl is substituted one to four times, for example once, twice or three times, especially once or twice, on the aromatic rings.

$C_1$–$C_{12}$alkoxy may comprise linear or branched radicals and is, for example, methoxy, ethoxy, propoxy, isopropoxy, n-butyloxy, sec-butyloxy, iso-butyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy, tert-butyloxy, preferably methoxy.

Halogen is fluorine, chlorine, bromine and iodine, especially fluorine, chlorine and bromine, preferably fluorine and chlorine.

Where $C_1$–$C_{20}$alkyl is substituted one or more times by halogen, there are, for example, 1 to 3 or 1 or 2 halogen substituents on the alkyl radical.

Where $R_7$ and $R_8$, together with the N atom to which they are attached, form a 5- or 6-membered ring which may additionally include O or S atoms, then the rings involved are, for example, saturated or unsaturated rings, for example aziridine, pyrrole, pyrrolidine, oxazole, thiazole, pyridine, 1,3-diazine, 1,2-diazine, piperidine or morpholine.

Examples of divalent aromatic hydrocarbon radicals are phenylene, stilbenylene, biphenylene, o-, m- and p-terphenylene, triphenylphenylene, naphthylene, binaphthylene, anthracenylene, phenanthrylene, pyrenylene, ferrocenylene, furanylene, thiophenylene, pyridinylene, quinolinylene or isoquinolinylene.

Naphthylene is

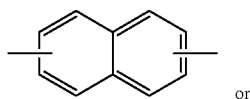

or

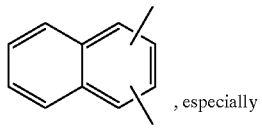

, especially

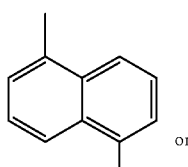

or

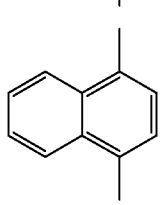

.

Stilbenylene is

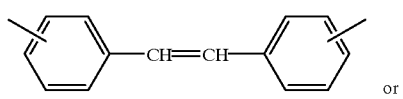

or

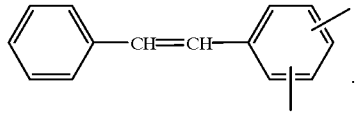

.

Biphenylene is

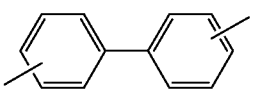

o-, m- or p-terphenylene are

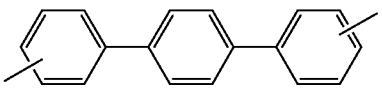

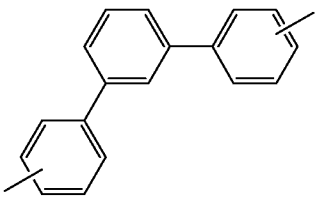

or

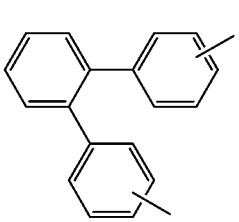

Triphenylphenylene is

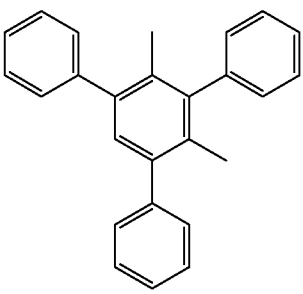

or

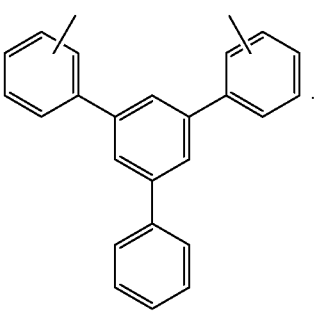

.

Binaphthylene is

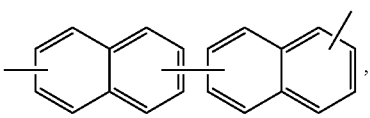

,

-continued
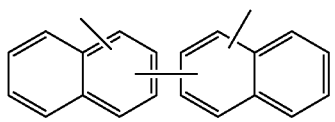, especially
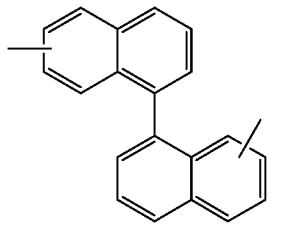 and
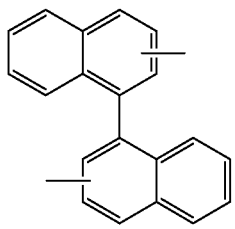.
Anthracylene is
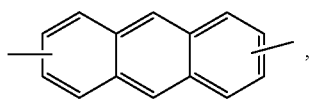,
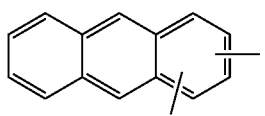,
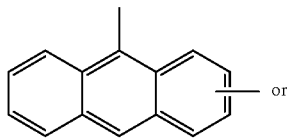 or
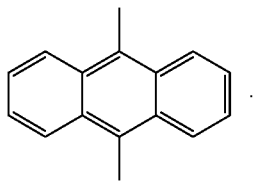.
Phenanthrylene is
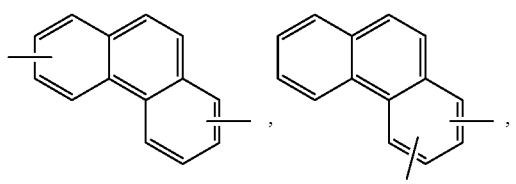,
-continued
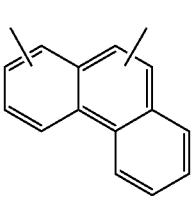 or 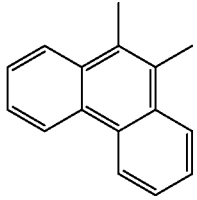.
Pyrenylene is
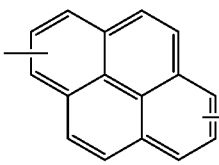, 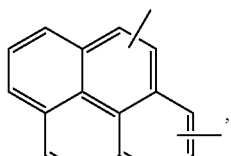,
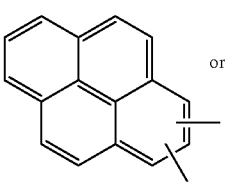 or 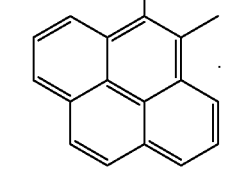.
Furanylene is
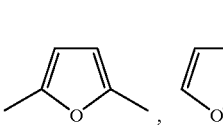 or 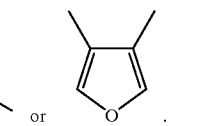.
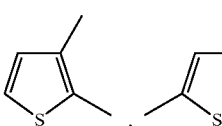 or 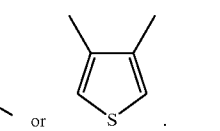.
Thiophenylene is
Pyridinylene is
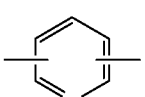.
Quinolinylene is
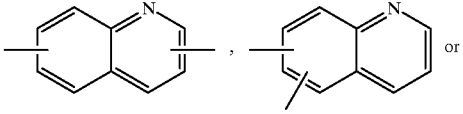 or

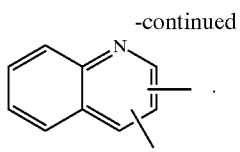

Isoquinolinylen is

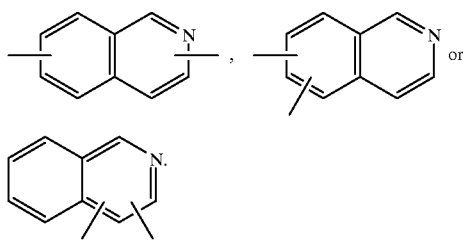

1,4-Duryl is

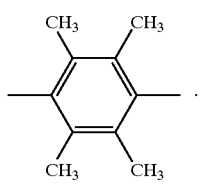

Substituted radicals phenylene, stilbenylene, biphenylene, o-, m- or p-terphenylene triphenylphenylene, naphthylene binaphthylene anthracylene phenanthrylene pyrenylene ferrocenylene furanylene, thiophenylene, pyridinylene, quinolinylene or isoquinolinylene are substituted one to four times, for example once, twice or three times, especially once or twice. Substituents on the 1,4-phenylene ring are in position 2, 3, 5 or 6, especially in position 2 or 3 of the phenyl ring. Substituents on the 1,3-phenylene ring are in position 2, 4, 5 or 6, especially in position 4 or 5 of the phenyl ring.

Radicals which are generally suitable as the counterion $G^+$ to the negative borate in the formula I are those which are able to form positive ions.

Examples of these are alkali metals, especially lithium or sodium, quarternary ammonium compounds, phosphonium, sulfonium and iodonium compounds, cationic transition metal complex compounds or dyes. For the unimolecular borate compounds of the formula I, G is preferably ammonium or tetraalkylammonium. Examples of tetraalkylammonium are, in particular, tetramethylammonium or tetrabutylammonium. However, trisalkylammonium ions, for example trimethylammonium, are also suitable. Other advantageous quarternary ammonium compounds are, for example, trimethylcetylammonium or cetylpyridinium. Also suitable are phosphonium and ammonium counterions of the formulae $^+PR_wR_xR_yR_z$ and $^+NR_wR_xR_yR_z$, where $R_w$, $R_x$, $R_y$, $R_z$ independently of one another are hydrogen, unsubstituted or substituted alkyl, cycloalkyl, alkenyl, phenyl or arylalkyl. Examples of substituents of these alkyl, cycloalkyl, alkenyl, phenyl and arylalkyl radicals are halide, hydroxyl, heterocycloalkyl (e.g. epoxy, aziridyl, oxetanyl, furanyl, pyrrolidinyl, pyrrolyl, thiophenyl,tetrahydrofuranyl, etc.), dialkylamino, amino, carboxyl, alkyl- and arylcarbonyl and aryloxy- and alkoxycarbonyl.

The tetravalent nitrogen may also be part of a 5- or 6-membered ring, in which case this ring may in turn be fused onto other ring systems. These systems may also include additional heteroatoms, for example S, N, O.

The tetravalent nitrogen may also be part of a polycyclic ring system, for example azoniapropellane. These systems may also contain further heteroatoms, for example S, N, O.

Also suitable are polyammonium salts and polyphosphonium salts, especially the bis salts, in which it is possible for the same substituents to be present as described above for the "mono" compounds.

The ammonium salts and phosphonium salts may also be substituted by neutral dyes (e.g. thioxanthenenes, thioxanthones, coumarins, ketocoumarins, etc.). Such salts are obtained by the reaction of the ammonium salts and phosphonium salts, substituted by reactive groups (e.g. epoxy, amino, hydroxyl, etc.), with appropriate derivatives of neutral dyes. Corresponding examples are described in EP-A 224 967 (Quantacure QTX).

Similarly, ammonium salts and phosphonium salts can also be substituted by colourless electron acceptors (e.g. benzophenones); examples of these are Quantacure ABQ

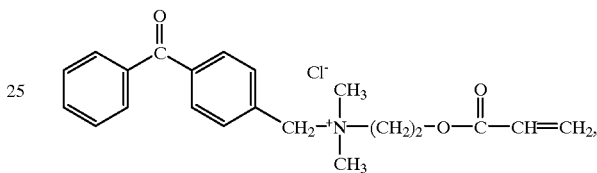

Quantacure BPQ

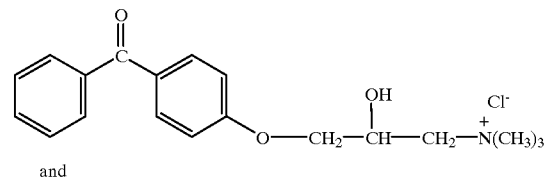

and

Quantacure BTC

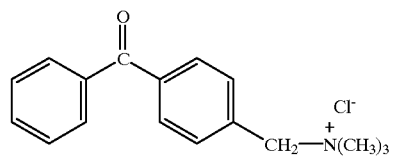

from International Biosynthetics.

The compounds of the formula I are reactive even when they do not contain as counterion any dye or cationic transition metal complex; in other words, they can be employed even in unimolecular form.

The invention therefore additionally provides compounds in which G is, in particular, a metal from group I of the Periodic Table in the first oxidation state, especially Na$^+$, K$^+$ or Li$^+$, or in which G is MgZ$_1^+$ or CaZ$_1^+$, in which Z$_1$ is a halogen or C$_1$–C$_4$alkoxy, or G is an ammonium salt, sulfonium salt or phosphonium salt.

An ammonium salt or phosphonium salt is, for example, R$_a$R$_b$R$_c$R$_d$N$^+$ or R$_a$R$_b$R$_c$R$_d$P$^+$, where R$_a$, R$_b$, R$_c$ and R$_d$ independently of one another are C$_1$–C$_{20}$alkyl, C$_3$–C$_{12}$cycloalkyl, C$_2$–C$_8$alkenyl, phenyl-C$_1$–C$_6$alkyl, naphthyl-C$_1$–C$_3$alkyl or phenyl.

The reactivity of the unimolecular photoinitiator compounds can of course be increased by adding coinitiators, for example dyes.

It is consequently also possible to use dye cations or cationic transition metal coordination complex compounds as counterion. These radicals then act as a coinitiator for the borate.

Examples of positive counterions $G^+$ to be employed in the compound of the formula I include the following ions:

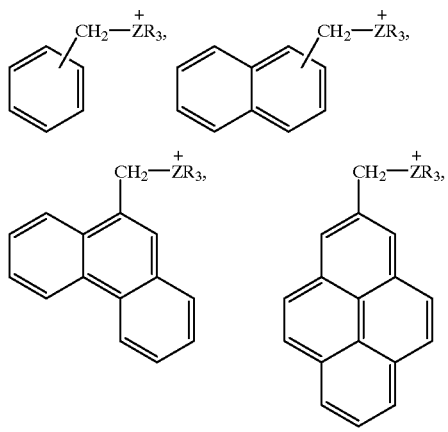

in which Z is P, S or N and R is an alkyl or aryl radical. Also suitable are compounds such as

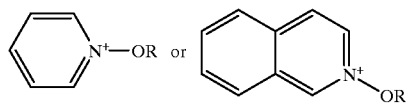

(described by Yagci et al. in J. Polym. Sci. Part A: Polymer Chem. 1992, 30, 1987 and Polymer 1993, 34(6), 1130), or compounds such as

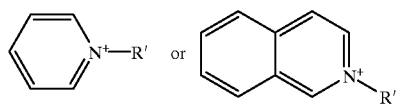

where R'=unsubstituted or substituted benzyl or phenacyl (described in JP-A Hei 7 70221). In these compounds, the aromatic rings in the pyridinium may also be substituted.

Tetraalkylammonium is, for example, $(C_1-C_{10}alkyl)_4N^+$, for example tetrahexylammonium, tetraoctylammonium, tetradecylammonium, tetrabutylammonium or tetramethylammonium. Preference is given to tetra($C_1-C_4$alkyl) ammonium, $N(C_1-C_4alkyl)^+$, in which $C_1-C_4$alkyl can have the definitions given above up to the corresponding number of carbon atoms. Examples of corresponding ammonium compounds are tetramethylammonium, tetraethylammonium, tetrapropylammonium or tetrabutylammonium, especially tetramethylammonium and tetrabutylammonium. Benzyl-tri($C_1-C_4$alkyl)ammonium is $C_6H_4-CH_2-N(C_1-C_4alkyl)_3^+$, in which $C_1-C_4$alkyl can have the same definitions as above up to the corresponding number of carbon atoms. Examples of such radicals are benzyltrimethylammonium, benzyltriethylammonium, benzyltripropylammonium and benzyltributylammonium, especially benzyltrimethylammonium and benzyltributylammonium.

Other positive counterions $G^+$ to the borate which are suitable for use are further onium ions, for example, iodonium or sulfonium ions. Examples of such counterions to the borate are radicals of the formula

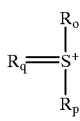

as described in EP-A 555 058 and EP-A 690 074. Also of interest as counterions are

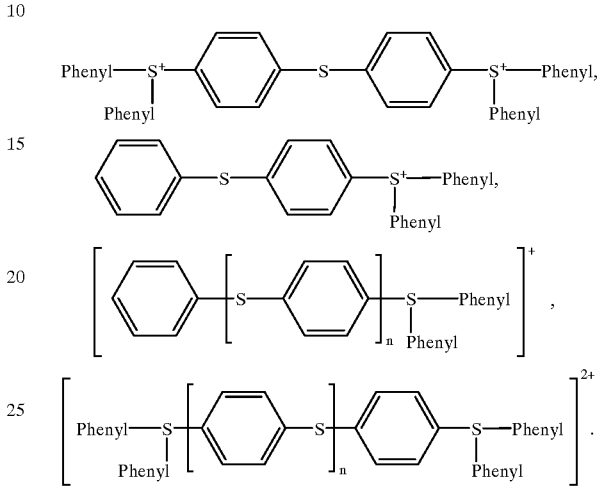

Further suitable counterions for the novel borates are cations of the formula

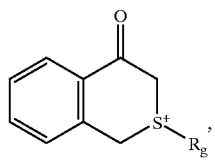

in which $R_g$ is an alkyl radical, especially ethyl, or benzyl, and where the aromatic ring can carry further substituents. Other suitable counterions are halonium ions, especially diaryliodonium ions, as described for example in EP-A 334 056 and EP-A 562 897.

However, cations of ferrocenium salts are also suitable, as described in EP-A 94915 and EP-A 109 851, for example

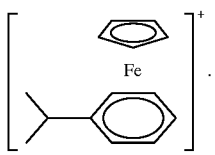

Other suitable onium cations, such as ammonium, phosphonium, sulfonium, iodonium, selonium, arsonium, tellonium and bismuthonium, are described, for example, in Japanese Patent Application Hei 6 266102.

Examples of cationic transition metal complex compounds which are suitable as counterions are described in U.S. Pat. No. 4,954,414. Of particular advantage are bis(2, 2'-bipyridine)(4,4'-dimethyl-2,2'-bipyridine)ruthenium, tris (4,4'-dimethyl-2,2'-bipyridine)ruthenium, tris(4,4'-dimethyl-2,2'-bipyridine)iron, tris(2,2',2"-terpyridine) ruthenium, tris(2,2'-bipyridine)ruthenium and bis(2,2'-bipyridine)(5-chloro-1,10-phenanthroline)ruthenium.

Examples of suitable dyes are for example cations of triarylmethanes, for example malachite green, indolines, thiazines, for example methylene blue, xanthones, thioxanthones, oxazines, acridines, cyanines, rhodamines, phenazines, for example safranin, preferably cyanines and thioxanthones.

Preferred compounds of the formulae I and I' are those in which $R_1$ and $R_2$ are identical.

Other compositions which are of interest are those in which, in the compounds of the formula I, $R_1$, $R_2$ and $R_3$ independently of one another are phenyl or aromatic hydrocarbon, with or without any heteroatoms, which radicals are unsubstituted or are substituted 1–5 times by unsubstituted or $OR_6$— or $R_7R_8N$-substituted $C_1$–$C_6$alkyl, $OR_6$, $R_6S(O)_p$, $R_6S(O)_2O$, $R_7R_8N$—, halogen and/or

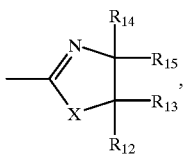

or the radicals $R_2$ and $R_3$ form bridges to produce structures of the formula II, IIa or IIb, $R_4$ is phenyl, $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl;

$R_{12}$, $R_{13}$, $R_{14}$, and $R_{15}$ independently of one another are H, $C_1$–$C_{12}$alkyl or phenyl, or the radicals $R_{12}$, $R_{13}$, $R_{14}$, and $R_{15}$ together form an aromatic ring to which further aromatic rings may be fused; and X is N or O.

Compositions worthy of emphasis are those in which, in the compound of the formula I or I', $R_4$ is $C_1$–$C_{12}$alkyl, allyl, cyclopentyl, cyclohexyl, benzyl or naphthylmethyl.

Particular preference is given to those compositions in which, in the compound of the formula I or I', $R_6$ is $C_1$–$C_4$alkyl, trifluoromethyl or phenyl which is unsubstituted or is substituted 1–5 times by $C_1$–$C_6$alkyl, $C_1$–$C_{12}$alkoxy and/or halogen.

Compositions which are of interest are those in which, in the compound of the formula I or I', $R_7$ and $R_8$ are $C_1$–$C_4$alkyl, phenyl or phenyl-$C_1$–$C_6$alkyl or, together with the N atom to which they are attached, are pyrrolidino, piperidino or morpholino.

Preference also is given to compositions in which, in the compound of the formula I, $R_1$ and $R_2$ are 2,6-di($C_1$–$C_6$alkyl)phenyl, 2,6-di($C_1$–$C_6$alkoxy)phenyl, 2,6-bis(trifluoromethyl)phenyl, 2,6-di(halo)phenyl, 2,4,6-tri($C_1$–$C_6$alkyl)phenyl, 2,4,6-tri($C_1$–$C_6$alkoxy)phenyl, 2,4,6-tris(trifluoromethyl)phenyl or 2,4,6-tri(halo)phenyl.

Preference is likewise given to compositions in which, in the compound of the formula I, $R_1$ and $R_2$ are mesityl.

Other preferred compositions are those in which, in the compound of the formula I, $R_1$ is 1-naphthyl, 2-($C_1$–$C_6$alkyl)naphth-1-yl, 1-anthracyl, 9-anthracyl or ferrocenyl.

Other compositions of interest are those in which, in the compound of the formula I, $R_1$ and $R_2$ are o-($C_1$–$C_6$alkyl)phenyl, o-(halo)phenyl, o-($C_1$–$C_6$alkoxy)phenyl or o-trifluoromethylphenyl.

Preference is additionally given to compositions in which, in the compound of the formula I, $R_1$ and $R_2$ are identical and are mono- to penta-$C_1$–$C_4$alkyl- and/or -halogen-substituted phenyl, naphthyl or anthracyl, $R_3$ is unsubstituted or halogen- or $C_1$–$C_4$alkyl-substituted phenyl, biphenyl, 1-naphthyl, 2-naphthyl, 9-anthracyl, 9-phenanthryl or 1-pyrenyl, $R_4$ is phenyl or $C_1$–$C_4$alkyl or $R_2$ and $R_3$ form a bridge to produce a structure of the formula II in which Y is a bond and G is tetramethylammonium, safranin O cation

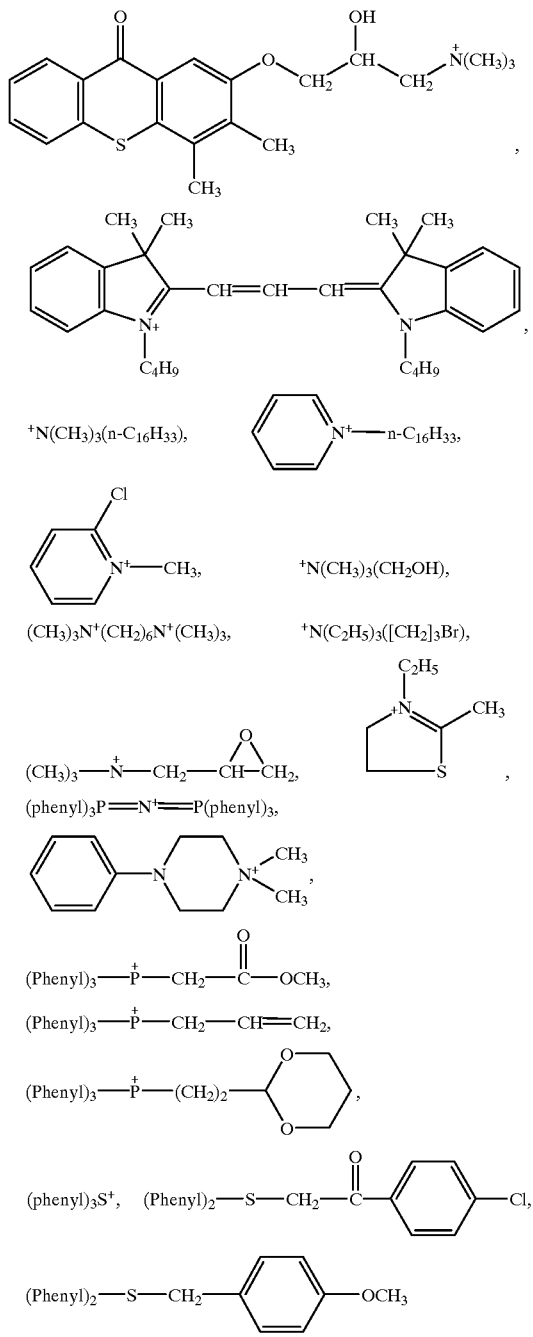

or a compound of the formula I' in which $R_{1a}$ is naphthylene and E is trimethylammonium or dimethylbenzylammonium.

The compounds of the formula I can be obtained, for example, by reacting triorganylboranes (A) with organometallic reagents, for example alkyllithium compounds or Grignard reagents:

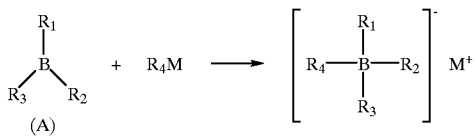

M is, for example, an alkali metal, such as Li or Na, or is MgX, where X is a halogen atom, especially Br.

Another possibility for preparing the compounds of the formula I is, for example, the reaction of alkyldihaloboranes or alkyldialkoxy- or alkyldiaryloxyboranes (B) with organometallic compounds such as, for example, Grignard reagents or lithium organyl compounds:

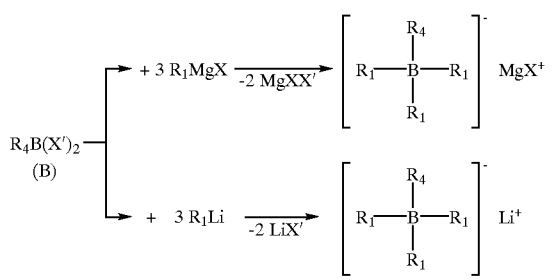

X is halogen, especially Br, X' is halogen, alkoxy or aryloxy. The definitions of the other radicals are as stated above.

Where G in formula I above is a positive radical other than lithium or magnesium, these compounds can be obtained, for example, by cation exchange reactions.

The reaction conditions when working with organometallic reagents are generally familiar to the skilled worker. For instance, reaction is expediently carried out in an inert organic solvent, for example an ether or aliphatic hydrocarbon, for example diethyl ether, tetrahydrofuran or hexane.

Examples of suitable organometallic reagents for preparing the novel polyborates are the lithium compounds of the corresponding aliphatic and aromatic hydrocarbon radicals. The preparation of Grignard reagents is familiar to the skilled worker and is widely described in textbooks and other publications.

Reaction with the organometallic reagent is expediently carried out with exclusion of air under an inert gas atmosphere, for example under nitrogen. In general the reaction is performed with cooling to 0° C. or below and subsequent heating to room temperature. It is expedient to stir the reaction mixture. The products are isolated and purified by methods likewise generally known to the skilled worker, for example chromatography, recrystallization, etc.

Where the novel compounds of the formula I contain a dye radical as cation, these compounds are prepared by the cation exchange reaction of a corresponding borate salt with a dye. Examples of the borate salts suitable for the exchange are the lithium, magnesium, sodium, ammonium and tetraalkylammonium salts.

Where the compounds of the formula I contain a transition metal complex as cation, these compounds are prepared by a method similar to that described in U.S. Pat. No. 4,954, 414, Column 7, Section 2.

Preparation of triorganylboranes (A): the preparation of some alkyldiarylboranes is described, for example, by A. Pelter et al. in Tetrahedron 1993, 49, 2965. The synthesis of some triarylboranes has been described by Doty et al. in J. Organomet. Chem. 1972, 38, 229, by Brown et al. in J. Organomet. Chem. 1981, 209, 1, by Brown et al. in J. Amer. Chem. Soc. 1957, 79, 2302, and by Wittig et al. in Chem. Ber. 1955, 88, 962. Preparation of aryldihaloboranes (B): the route to some alkyldihaloboranes (B) has been shown, for example, by Brown et al. in JACS 1977, 99, 7097 and in U.S. Pat. No. 3,083,288. Furthermore, Mikailov et al. in Zh. Obshch. Khim. 1959, 29, 3405, and Tuchagues et al. in Bull. Chim. Soc. France, 1967, 11, 4160, describe the preparation of such compounds. The preparation of phenyldifluoroborane has been presented by Nahm et al. in J. Organomet. Chem. 1972, 35, 9.

The alkyldialkoxy- and alkyldiaryloxyboranes, for example, can be prepared by various published procedures, for example Brown et al. Organometallics 1983, 2, 1316; Brown et al., Organometallics 1992, 11 3094; Brown et al., J. Org. Chem. 1980, 2, 1316. The boranes required as starting materials for the novel compounds can be obtained, for example, in accordance with one of the published methods mentioned above.

The invention extends to compounds of the formulae Ia and Ia'

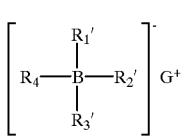

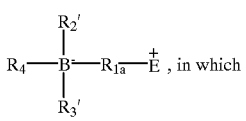

$R_1'$ and $R_2'$ independently of one another are phenyl which is substituted in at least one ortho-position to the bond to the boron atom by $C_1$–$C_{20}$alkyl, $C_2$–$C_{20}$alkyl which is interrupted by one or more radicals O, $S(O)_p$ or $NR_5$, $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$, CN and/or

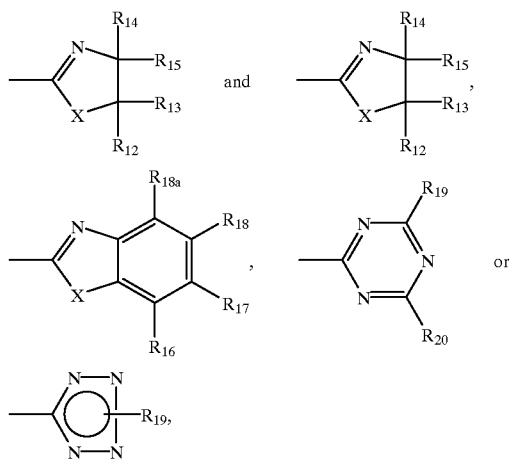

or the radicals $R_1'$ and $R_2'$ form bridges to produce structures of the formula II, IIa or IIb

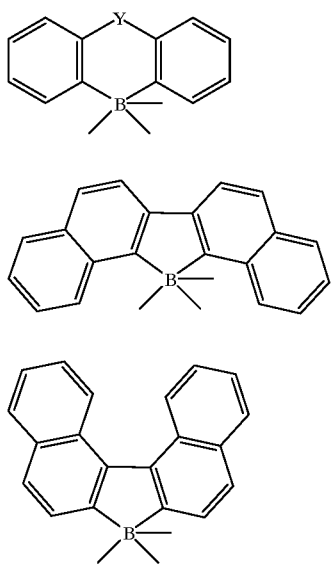

(II)

(IIa)

(IIb)

where the aromatic rings in the formula II are unsubstituted or are substituted by $C_1$–$C_{20}$alkyl, $C_2$–$C_{20}$alkyl which is interrupted by one or more radicals O, $S(O)_p$ or $NR_5$, $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, halogen, $R_9R_{10}P(O)_q$ and/or $R_9R_{10}R_{11}Sn$;

$R_{1a}'$ is a divalent aromatic hydrocarbon radical which is unsubstituted or is substituted by $C_1$–$C_6$alkyl, $OR_6$, $S(O)_pR_6$, $OS(O)_2R_6$, $NR_8R_7$, $C(O)OR_6$, $C(O)NR_8R_7$, $C(O)R_9$, $SiR_9R_{10}R_{11}$ or halogen, or $R_{1a}'$ is phenyl-$C_1$–$C_6$alkylene;

$R_3'$ is a bulky aromatic radical, $R_4$ is phenyl, $C_1$–$C_{20}$alkyl, $C_2$–$C_{20}$alkyl interrupted by one or more radicals O, $S(O)_p$ or $NR_5$, or is $C_3$–$C_{12}$cycloalkyl, $C_2$–$C_8$alkenyl, phenyl-$C_1$–$C_6$alkyl or naphthyl-$C_1$–$C_3$alkyl, where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsubstituted or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$, and/or CN;

Y is $(CH_2)_n$, CH=CH, C(O), $NR_5$, O, $S(O)_p$ or

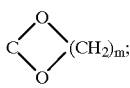

n is 0, 1 or 2;
m is 2 or 3;
p is 0, 1 or 2;
q is 0 or 1;
E is $R_{21}R_{22}R_{23}P$, $R_7R_{7a}R_8N$ or $R_6R_{6a}S$;
$R_5$ is hydrogen, $C_1$–$C_{12}$alkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy and/or halogen;
$R_6$ and $R_{6a}$ independently of one another are $C_1$–$C_{12}$alkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy and/or halogen;

$R_7$, $R_{7a}$ and $R_8$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy and/or halogen, or $R_7$ and $R_8$, together with the N atom to which they are attached, form a 5- or 6-membered ring which may additionally contain O or S atoms;

$R_9$, $R_{10}$ and $R_{11}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy and/or halogen; $R_{12}$, $R_{13}$, $R_{14}$ and $R_{15}$ independently of one another are hydrogen, unsubstituted or $C_1$–$C_{12}$alkoxy-substituted $C_1$–$C_{12}$alkyl, unsubstituted or mono- to penta-$C_1$–$C_6$alkyl-, $C_1$–$C_{12}$alkoxy- or -halogen-substituted phenyl-$C_1$–$C_6$alkyl or are unsubstituted or mono- to penta-$C_1$–$C_6$alkyl, -$C_1$–$C_{12}$alkoxy- or -halogen-substituted phenyl, or the radicals $R_{12}$, $R_{13}$, $R_{14}$ and $R_{15}$ together form an aromatic ring to which further aromatic rings may be fused;

$R_{21}$, $R_{22}$ and $R_{23}$ independently of one another are $C_1$–$C_{12}$alkyl, $C_2$–$C_{12}$alkenyl or $C_3$–$C_{12}$cycloalkyl, where the radicals $C_1$–$C_{12}$alkyl, $C_2$–$C_{12}$alkenyl and $C_3$–$C_{12}$cycloalkyl are unsubstituted or are substituted by $R_6OCO$ or CN, or $R_{21}$, $R_{22}$ and $R_{23}$ are unsubstituted or mono- to penta-$C_1$–$C_6$alkyl-, -$C_1$–$C_{12}$alkoxy- or -halogen-substituted phenyl-$C_1$–$C_6$alkyl or are unsubstituted or mono- to penta-$C_1$–$C_6$alkyl-, -$C_1$–$C_{12}$alkoxy- or -halogen-substituted phenyl; and G is a radical which is able to form positive ions.

Preferred compounds are those in which $R_3'$ is 1- or 2-naphthyl, binaphthyl, anthracyl, phenanthryl, pyrenyl, quinolyl, isoquinolyl, biphenyl, o-, m- or p-terphenyl or triphenylphenyl.

The definitions of the radicals $R_1'$, $R_2'$ and $R_3'$ are exactly as given above for $R_1$, $R_2$ and $R_3$.

In accordance with the invention the compounds of the formula Ia can be used as photoinitiators for the photopolymerization of ethylenically unsaturated compounds or of mixtures comprising such compounds.

Compounds of the formula Ia which do not contain a dye radical as counterion can be employed as unimolecular photoinitiators.

Compounds which are particularly in accordance with the invention, therefore, are those of the formula Ia, in which G is a metal from group I of the Periodic Table in the first oxidation state, especially $Na^+$, $K^+$ or $Li^+$, or G is $MgZ_1^+$ or $CaZ_1^+$, in which $Z_1$ is a halogen or $C_1$–$C_4$alkoxy, or G is an ammonium salt, sulfonium salt or phosphonium salt.

In order to increase the reactivity the compounds can of course also be used in combination with at least one coinitiator or electron acceptor (c).

Use may also be made in combination with another photoinitiator and/or other additives.

The novel composition as well may comprise, in addition to components (a) and (b), other photoinitiators (d) and/or other additives, and also at least one coinitiator or electron acceptor (c).

Examples of dyes suitable as electron acceptor which can be added as coinitiators are described in U.S. Pat. No. 5,151,520. Examples are triarylmethanes, for example malachite green, indolines, thiazines, for example methylene blue, xanthones, thioxanthones, oxazines, acridines or phenazines, for example safranin.

As coinitiator is it also possible to use the above-described transition metal complex compounds or onium ion compounds.

Cationic, neutral or anionic dyes can be used as coinitiators for the novel compounds. Particularly suitable cationic dyes are malachite green, methylene blue, safranin O, rhodamines of the formula III

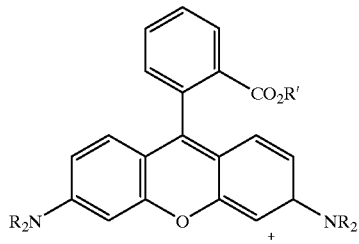

(III)

in which R and R' are alkyl or aryl radicals, examples being rhodamine B, rhodamine 6G or violamine R, and also sulforhodamine B or sulforhodamine G.

Other suitable dyes are fluorones, as described for example by Neckers et al. in J. Polym. Sci., Part A, Poly. Chem, 1995, 33, 1691–1703.

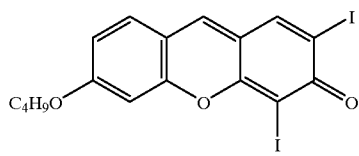

is particularly advantageous.

Examples of further suitable dyes are cyanines of the formula IV

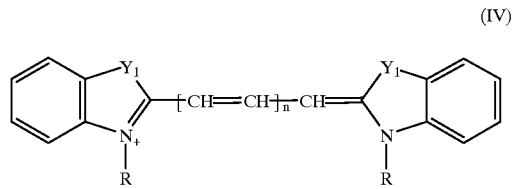

(IV)

in which R=alkyl; n=0,1,2,3 or 4 and $Y_1$=CH=CH, N—$CH_3$, $C(CH_3)_2$, O, S or Se. Preferred cyanines are those in which $Y_1$ in the above formula IV is $C(CH_3)_2$ or S.

The following dye compounds are also suitable as coinitiators:

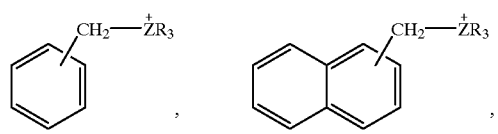

-continued

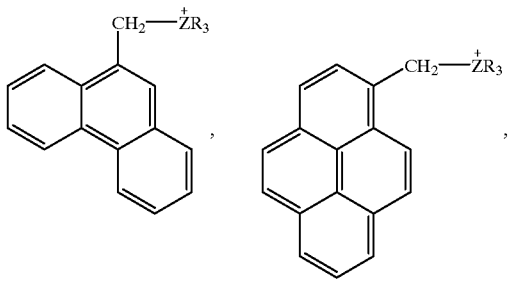

in which Z is P, S or N and R is an alkyl or aryl radical. Preferred compounds of the above formulae are those in which $ZR_3$ is $N(CH_3)_3$, $N(C_2H_5)_3$ or $P(C_6H_5)_3$.

Also suitable are compounds such as, for example,

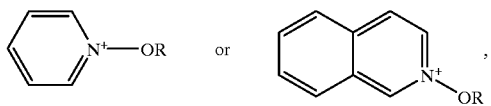

as described for example by Yagci et al. in J. Polym. Sci. Part A: Polymer Chem. 1992, 30, 1987 and Polymer 1993, 34(6), 1130, or such as, for example,

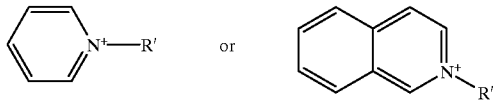

where R'=unsubstituted or substituted benzyl or phenacyl, described in JP-A Hei 7 70221. The abovementioned pyridinium compounds may also be substituted in the aromatic pyridinium ring.

Other suitable dyes can be found, for example, in U.S. Pat. No. 4,902,604. These are azulene dyes. Of particular advantage as coinitiators for the novel compounds are the compounds 1–18 listed in columns 10 and 11 of this patent in the table.

Examples of further suitable dyes are merocyanine dyes, as described in U.S. Pat. No. 4,950,581 from column 6, line 20 to column 9, line 57.

As coinitiators for the novel compounds and compositions it is also possible to use coumarin compounds. Examples of these are given in U.S. Pat. No. 4,950,581 in column 11, line 20 to column 12, line 42.

Other suitable coinitiators are xanthones or thioxanthones as described, for example, in U.S. Pat. No. 4,950,581, column 12, line 44 to column 13, line 15.

Anionic dye compounds can also be employed, for example, as coinitiators. For instance, Rose Bengal, eosine or fluorescein are also suitable. Other suitable dyes, for example from the triarylmethane class or azo class, are described in U.S. Pat. No. 5,143,818.

Further suitable coinitiators or electron acceptors (c) are benzopteridinediones (described in JP Hei 02 113002), substituted benzophenones (for example Michler's ketone, Quantacure ABQ, Quantacure BPQ and Quantacure BTC from International Biosynthetics), trichloromethyltriazines (described in JP Hei 01 033548), metal complexes (described in JP Hei 04 261405), porphyrins (described in JP Hei 06 202548 and JP Hei 06 195014), coumarins and ketocoumarins (described in U.S. Pat. No. 4,950,581 and JP Hei 06 175557), p-aminophenyl compounds (described in EP-A 475153), xanthenes (described in JP Hei 06 175566) or pyrylium, thiopyrylium and selenopyrylium dyes (described in JP Hei 06 175563).

Other suitable electron acceptor compounds and coinitiators are given later on below.

Other compositions of interest are those in which a readily reducible compound, especially a halogenated hydrocarbon, is employed as a further additive.

Halogenated hydrocarbons are suitable readily reducible compounds. Examples thereof are, in particular,

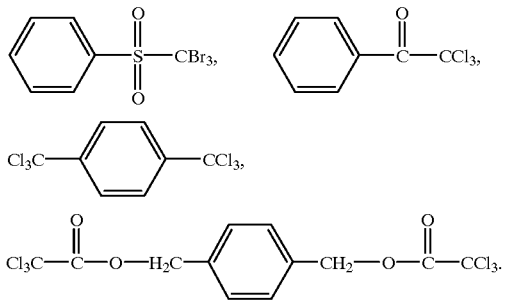

The term readily reducible compound in this context also refers to compounds as described in U.S. Pat. No. 4,950,581, and includes, for example, iodonium salts, sulfonium salts, organic peroxides, compounds containing carbon-halide bonds (trichloromethyltriazines), heterocyclic sulfur compounds and other photoinitiators ($\alpha$-amino ketones). Examples of other additives are heterocycles as described in the Patents and Patent Applications U.S. Pat. No. 5,168,032, JP 02 244050, JP 02 054268, JP 01 017048 and DE 383308. Examples of further additives are aromatic imines, described in U.S. Pat. No. 5,079,126, and aromatic diazo compounds, described in U.S. Pat. No. 5,200,292 (for example iminoquinone diazides), thiols, described in U.S. Pat. No. 4,937,159, and thiols and N,N-dialkylanilines described in U.S. Pat. No. 4,874,685. It is also possible to employ two or more of the abovementioned coinitiators or electron acceptors and additives in combination.

The invention additionally provides a composition comprising in addition to components (a) and (b) at least one compound of the formula XI

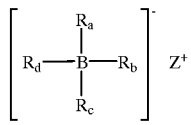

(XI)

in which $R_a$, $R_b$, $R_c$ and $R_d$ independently of one another are $C_1$–$C_{12}$alkyl, trimethylsilylmethyl, phenyl, another aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl or saturated or unsaturated heterocyclic radicals, wherein the radicals phenyl, another aromatic hydrocarbon, phenyl-$C_1$–$C_6$alkyl or saturated or unsaturated heterocyclic radical are unsubstituted or are substituted 1–5 times by unsubstituted or $OR_6$— or $R_7R_8N$-substituted $C_1$–$C_{20}$alkyl, $C_2$–$C_{20}$alkyl which is interrupted by one or more radicals O, $S(O)_p$ or $NR_5$, $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen or $R_9R_{10}P(O)_q$, CN;

p is 0, 1 or 2;

q is 0 or 1;

$R_5$ is hydrogen, $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;

$R_6$ is unsubstituted or halogen-substituted $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen;

$R_7$ and $R_8$ independently of one another are unsubstituted or $C_1$–$C_{12}$alkoxy-, halogen-, OH—, $COOR_6$— or CN-substituted $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen, or $R_7$ and $R_8$, together with the N atom to which they are attached, form a 5- or 6-membered ring which may additionally contain O or S atoms;

$R_9$, $R_{10}$ and $R_{11}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy and/or halogen; and Z is a radical which is able to form positive ions, especially alkali metals, ammonium or tetraalkylammonium.

The definitions of $C_1$–$C_{12}$alkyl, aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl, saturated or unsaturated heterocyclic radical, radical which is able to form positive ions, alkali metal and tetraalkylammonium, as well as $R_5$–$R_{11}$ are as indicated above for the formula I, I', Ia or Ia'.

The invention additionally provides a composition comprising at least one borate of the formula I, I', Ia or Ia' and at least one dye which changes or loses its colour during or after irradiation, it also being possible for this dye, as cation, to be a constituent of the compound of the formula I, I', Ia or Ia'. Examples of such dyes are cyanine or pyrylium dyes.

As already mentioned, it is advantageous to combine the novel borate compounds with coinitiators, for example sensitizers (=energy transfer compounds). In this context, additionally and particularly, combinations with two or more different sensitizers, for example mixtures of the novel borate compounds with onium salts and thioxanthones or coumarins with dyes, are highly effective. Preferred onium salts in these mixtures are diphenyliodonium hexafluorophosphate, (p-octyloxy-phenyl)(phenyl)iodonium hexafluorophosphate, or corresponding other anions of these compounds, for example the halides; and also sulfonium salts, for example triarylsulfonium salts (Cyracure® UVI 6990, Cyracure® UVI-6974 from Union Carbide; Degacure® KI 85 from Degussa or SP-150 und SP-170 from Asahi Denka). Preference is given, for example, to a mixture of the novel borate compounds with diphenyliodonium hexafluorophosphate and isopropylthioxanthone, to a mixture of the novel borate compounds with (p-octyloxyphenyl)(phenyl)iodonium hexafluorophosphate and isopropylthioxanthone, and to a mixture of the novel borate compounds with

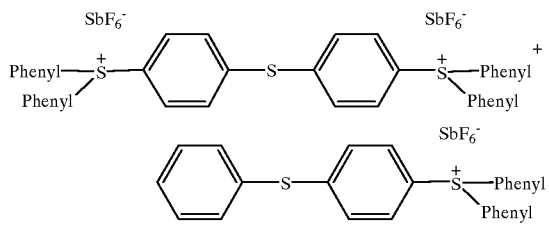

(=Cyracure® UVI-6974) and isopropylthioxanthone.

However, it is particularly advantageous to add yet another photoinitiator, of the α-amino ketone type, to the above-mentioned mixtures. For example, mixtures of the novel borates with onium salts and thioxanthones or dyes and α-amino ketones are highly effective. A preferred example is the mixture of the novel borate compounds with diphenyliodonium hexafluorophosphate or (p-octylphenyl)(phenyl) iodonium hexafluorophosphate, isopropylthioxanthone and (4-methylthiobenzoyl)methyl-1-morpholino-ethane. A particularly suitable borate compound in these mixtures is tetramethylammonium methyl dimesityl(1-naphthyl) borate.

The invention therefore also provides compositions comprising in addition to components (a) and (b) at least one neutral, anionic or cationic dye or a thioxanthone compound and an onium compound, and those compositions comprising in addition a free-radical photoinitiator, especially an α-amino ketone compound.

The unsaturated compounds of component (a) may include one or more olefinic double bonds. They may be of low (monomeric) or high (oligomeric) molecular mass. Examples of monomers containing a double bond are alkyl or hydroxyalkyl acrylates or methacrylates, such as methyl, ethyl, butyl, 2-ethylhexyl or 2-hydroxyethyl acrylate, isobornyl acrylate, methyl methacrylate and ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride and vinylidene chloride.

Examples of monomers containing two or more double bonds are the diacrylates of ethylene glycol, propylene glycol, neopentyl glycol, hexamethylene glycol and of bisphenol A, and 4,4'-bis(2-acryloyloxyethoxy) diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanu rate or tris(2-acryloylethyl) isocyanurate.

Examples of polyunsaturated compounds of relatively high molecular mass (oligomers) are acrylicized epoxy resins, acrylicized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxybiphenyl, 2,2-di(4-hydroxyphenyl)propane, and also novolaks and resols. Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one or with different unsaturated carboxylic acids, and in partial esters the free hydroxyl groups may be modified, for example etherified or esterified with other carboxylic acids. Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis (methacrylamidopropoxy)ethane, β-methacrylamidoethyl methacrylate and N-[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth) acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth) acrylic acid, or may be homo- and copolymers of (meth) acrylates which are esterified with hydroxyalkyl (meth) acrylates.

The photopolymerizable compounds can be used alone or in any desired mixtures. It is preferred to use mixtures of polyol (meth)acrylates.

Binders as well can be added to these novel compositions, and this is particularly expedient when the photopolymerizable compounds are liquid or viscous substances. The quantity of binder may, for example, be 5–95%, preferably 10–90% and especially 40–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5000 to 2000000, preferably 10000 to 1000000. Examples are: homo- and copolymers of acrylates and methacrylates, for example copolymers of methyl methacrylate/ethyl acrylate/methacrylic acid, poly (alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene chloride copolymers, copolymers of vinylidene chloride with acrylonitrile, methyl methacrylate and vinyl acetate, polyvinyl acetate, copoly(ethylene-vinyl acetate), polymers such as polycaprolactam and poly (hexamethyleneadipamide), and polyesters such as poly (ethylene glycol terephthalate) and poly(hexamethylene glycol succinate).

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins. The use of heat-curable resins at the same time is important for use in systems known as hybrid systems, which in a first stage are photopolymerized and in a second stage are crosslinked by means of thermal aftertreatment.

The invention additionally provides compositions which in addition to components (a) and (b) comprise at least one coinitiator or electron acceptor (c), for example a neutral, cationic or anionic dye or a UV absorber.

Suitable dyes (c) are described above. Other suitable examples are benzoxanthene, benzothioxanthene, pyronine or porphyrin dyes.

Particular preference is given to compositions having cyanide derivatives as dyes. Especially preferred cyanides are those of the formula IV in which n=1–4, $Y_1=C(CH_3)_2$ or S and $R=C_1-C_{10}$alkyl.

Examples of UV absorbers which are suitable as coinitiator or electron acceptor (c) are thioxanthone derivatives, coumarins, benzophenone, benzophenone derivatives or derivatives of hexaarylbisimidazole (HABI). Examples of suitable hexaarylbisimidazole derivatives are described in U.S. Pat. Nos. 3,784,557, 4,252,887, 4,311,783, 4,459,349, 4,410,621 and 4,622,286. Of particular interest are 2-o-chlorophenyl-substituted derivatives, such as 2,2'-bis(o-chlorophenyl)-4,4',5,5'-tetraphenyl-1,1'-bisimidazole. Other UV absorbers suitable in this context are, for example, polycyclic aromatic hydrocarbons, for example anthracene or pyrene, and the triazines described in EP-A-137 452, in DE-A-27 18 254 and in DE-A-22 43 621. Further suitable triazines can be found in U.S. Pat. No. 4,950,581, column 14, line 60 to column 18, line 44. Of particular interest are trihalomethyltriazines, for example 2,4-bis (trichloromethyl)-6-(4-styrenephenyl)-s-triazine.

In addition to the photoinitiator the photopolymerizable mixtures may include various additives. Examples of these are thermal inhibitors, which are intended to prevent premature polymerization, examples being hydroquinone, hydroquinone derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface at the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS).

Examples of such UV absorbers and light stabilizers are 1.2-(2'-hydroxyyhenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-yl-phenyl 2.2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

3. Esters of substituted or unsubstituted benzoic acids, for example 4-tert-butylphenyl salicylate, phenyl salicylate, octylphenyl salicylate, dibenzoylresorcinol, bis(4-tertbutylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carboxymethoxy-β-methoxycinnamate and N-(β-carbomethoxy-β-cyanovinyl)-2-methylindoline.

5. Sterically hindered amines, for example bis-(2,2,6,6-tetramethylpiperidyl) sebacate, bis-(2,2,6,6-tetramethylpiperidyl) succinate, bis-(1,2,2,6,6-pentamethylpiperidyl) sebacate, bis(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6, 6-tetramethyl-4-piperidyl)hexamethylendiamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropylamino)ethane, condensation product of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2, 5-dione and 3-dodecyl-1-(1,2,2,6,6-pentamethyl-4-piperidyl)pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanalides.

7.2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxy-propyloxy)phenyl]-4,6-bis(2,4-dimethyl-phenyl)-1,3,5-triazine, 2-[2-hydroxy-4-(2-hydroxy- 3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxy-phenyl]-4,6-bis(2,4-dimethylphenyl)-1,3,5-triazine.

8. Phosihites and phosihonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris-(2,4-di-tert-butylphenyl) phosphite, diisodecyl pentaerythrityl diphosphite, bis(2,4-di-tert-butylphenyl) pentaerythrityl diphosphite, bis-(2,6-di-tert-butyl-4-methylphenyl) pentaerythrityl diphosphite, bis-isodecyloxy pentaerythrityl diphosphite, bis-(2,4-di-tert-butyl-6-methylphenyl) pentaerythrityl diphosphite, bis-(2,4,6-tri-tert-butylphenyl) pentaerythrityl diphosphite, tristearyl sorbityl triphosphite, tetrakis(2,4-di-tert-butylphenyl)-4,4'-biphenylenediphosphonite, 6-isooctyloxy-2,4,8,10-tetratert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis-(2,4-di-tert-butyl-6-methylphenyl) methylphosphite and bis(2,4-di-tert-butyl-6-methylphenyl) ethyl phosphite.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP-A-339 841. Other accelerators, coinitiators and autoxidizers are, for example, thiols, thioethers, disulfides and phosphines, phosphonium salts or phosphine oxides as described, for example, in EP-A-438 123 and GB-2 180 358 and JP Hei 06 268309.

The photopolymerization can also be accelerated by adding further photosensitizers which shift or broaden the spectral sensitivity. These are, in particular, aromatic carbonyl compounds such as, for example, benzophenone, thioxanthone, anthraquinone and 3-acylcoumarin derivatives and 3-(aroylmethylene)thiazolines, but also eozine, rhodamine and erythrosine dyes.

The curing process can be assisted by, in particular, compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP-A-245 639.

Further customary additives, depending on the intended use, are fluorescent whiteners, fillers, pigments, dyes, wetting agents and levelling assistants. In order to cure thick and pigmented coatings it is appropriate to add glass microspheres or pulverized glass fibres, as described for example in U.S. Pat. No. 5,013,768.

The invention also provides compositions comprising as component (a) at least one ethylenically unsaturated photopolymerizable compound which is emulsified or dissolved in water.

Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have a content of from 0.01 to 1.0 mol of polymerizable double bonds per 100 g of prepolymer and an average molecular weight of, for example, at least 400, in particular from 500 to 10000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth) acrylates and of acrylic copolymers which contain u.,B-ethylenically unsaturated acrylic radicals, as are described in EP-A-12 339. Mixtures of these prepolymers can likewise be used. Also suitable are the polymerizable prepolymers described in EP-A-33 896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth) acrylate polymers, are described in EP-A-41 125, and suitable water-dispersible, radiation-curable prepolymers of urethane acrylates can be found in DE-A-29 36 039.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, matting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone and cellulose ethers. Emulsifiers which can be used are nonionic emulsifiers and, if desired, ionic emulsifiers as well.

In certain cases it may be of advantage to use mixtures of two or more of the novel photoinitiators. It is of course also possible to use mixtures with other known photoinitiators, for example mixtures with benzophenone, acetophenone derivatives, for example α-hydroxycycloalkyl phenyl ketones, dialkoxyacetophenones, α-hydroxy- or α-aminoacetophenones, 4-aroyl-1,3-dioxolanes, benzoin alkyl ethers and benzil ketals, monoacyl phosphine oxides, bisacylphosphine oxides, ferrocenes, xanthones, thioxanthones, anthraquinones or titanocenes.

Examples of particularly suitable photoinitiators are: 1-(4-dodecylbenzoyl)-1-hydroxy-1-methylethane, 1-(4-isopropylbenzoyl)-1-hydroxy-1-methylethane, 1-benzoyl-1-hydroxy-1-methylethane, 1-[4(2-hydroxyethoxy)-benzoyl]-1-hydroxy-1-methylethane, 1-[4(acryloyloxyethoxy) benzoyl]-1-hydroxy-1-methylethane, diphenyl ketone, penyl-1-hydroxy-cyclohexyl ketone, (4-morpholinobenzoyl)-1-benzyl-1-dimethylaminopropane, 1-(3,4-di-methoxyphenyl)-2-benzyl-2-dimethylamino-butan-1-one, (4-methylthiobenzoyl)-1-methyl-1-morpholinoethane, benzil dimethyl ketal, bis (cyclopentadienyl)-bis(2,6-difluoro-3-pyrryl-phenyl) titanium, cyclopentadienyl-arene-iron(II) complex salts, for example ($\eta^6$-iso-propylbenzene)($\eta^5$-cyclopentadienyl)iron (II) hexafluorophosphate, trimethylbenzoyldiphenylphosphine oxide, bis(2,6-dimethoxy-benzoyl)-(2,4,4-trimethyl-pentyl)phosphine oxide, bis(2,4,6-trimethylbenzoyl)-2,4-dipentoxyphenylphosphine oxide or bis(2,4,6-trimethylbenzoyl)phenylphosphine oxide. Other suitable additional photoinitiators can be found in U.S. Pat. No. 4,950,581 column 20, line 35 to column 21, line 35.

Also suitable are triazine compounds, for example the triazines described in EP-A-137 452, in DE-A-27 18 254 and in DE-A-22 43 621. Further suitable triazines can be found in U.S. Pat. No. 4,950,581, column 14, line 60 to column 18, line 44. There is particular interest in trihalomethyltriazines, for example 2,4-bis (trichloromethyl)-6-(4-styrylphenyl)-s-triazine. Where the novel photoinitiators are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17–25), aromatic sulfonium or iodonium salts (as described for example in U.S. Pat. No. 4,950,581, column 18, line 60 to column 19, line 10) or cyclopentadienyl-arene-iron(II)

complex salts, for example ($\eta^6$-iso-propylbenzene)($\eta^5$-cyclopentadien-yl)iron(II) hexafluorophosphate.

The invention therefore also provides, as already mentioned above, compositions containing in addition to photoinitiator (b) at least one other photoinitiator (d) and/or other additives.

The photopolymerizable compositions comprise the photoinitiator (b), and/or the components (b)+(d), expediently in a quantity of from 0.05 to 15% by weight, preferably from 0.1 to 5% by weight, based on the composition.
(The quantities indicated relate to the overall quantity of photoinitiator in the composition.)
Particular preference is given to compositions containing as photoinitiator (d) a titanocene, a ferrocene, a benzophenone, a benzoin alkyl ether, a benzil ketal, a 4-aroyl-1,3-dioxolane, a dialkoxyacetophenone, an α-hydroxy- or α-aminoacetophenone, an α-hydroxycycloalkyl phenyl ketone, a xanthone, a thioxanthone, an anthraquinone or a mono- or bisacylphosphine oxide, or mixtures thereof, as additional photoinitiator.

The photopolymerizable compositions can be used for various purposes, for example as printing ink, as a clear finish, as a white finish, for example for wood or metal, as a coating material, inter alia for paper, wood, metal or plastic, as a daylight-curable coating for roadmarking and the marking of buildings, for photographic reproduction techniques, for holographic recording materials, for image recording techniques or to produce printing plates which can be developed with organic solvents or with aqueous alkalis, for producing masks for screen printing, as dental filling compositions, as adhesives, including pressure-sensitive adhesives, as laminating resins, as etch resists or permanent resists, and as solder masks for electronic circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may if desired contain glass fibres and/or other fibres and other auxiliaries) and other thick-layered compositions, for coating or sealing electronic components, or as coatings for optical fibres.
The novel compounds may additionally be employed as initiators for emulsion polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent. Unsaturated polyester resins are usually used in two-component (two-pack) systems together with a monounsaturated monomer, preferably with styrene. For photoresists, specific one-component systems are often used, for example polymaleimides, polychalcones or polyimides, as described in DE-A-23 08 830.

The novel compounds and mixtures thereof can also be used as free-radical photoinitiators or photoinitiating systems for radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings may also comprise binders as are described, for example, in DE-A-42 28 514 and in EP-A-636 669. Free-radically, UV-curable powder coatings can also be formulated by mixing unsaturated polyester resins with solid acrylates, methacrylates or vinyl ethers and with a novel photoinitiator (or photoinitiator mixture). The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiators, the powder coating formulations may also include UV absorbers. Appropriate examples are listed above in sections 1.–8.

The novel photocurable compositions are suitable, for example, as coating materials for substrates of all kinds, for example wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate a reproduced image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 μm to more than 100 μm.

The novel radiation-sensitive compositions find application as negative resists, having a very high sensitivity to light and being able to be developed in an aqueous alkaline medium without swelling. They are suitable as photoresists for electronics (electroplating resist, etch resist, solder resist), the production of printing plates, such as offset printing plates or screen printing, for use in chemical milling or as a microresist in the production of integrated circuits. The possible layer supports, and the processing conditions of the coated substrates, are just as varied.

The compounds according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recording include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 μm to 10 μm, while for printed circuits it is from 1.0 μm to about 100 μm.

Following the coating of the substrates, the solvent is removed, generally by drying, to leave a coat of the photoresist on the substrate.

The term "imagewise exposure" includes both exposure through a photomask comprising a predetermined pattern, for example a slide, exposure by means of a laser beam, which for example is moved under computer control over the surface of the coated substrate and in this way produces an image, and irradiation with computer-controlled electron beams.

Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photocurable composition may additionally be used in a process for producing printing plates or photoresists as is described, for example, in DE-A-40 13 358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the binder is a critical factor for the production rate of graphic products, and should be in the order of fractions of seconds. UV-curable inks are particularly important for screen printing.

As already mentioned above, the novel mixtures are highly suitable for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent.

Another field where photocuring is employed is the coating of metals, in the case, for example, of the coating of metal plates and tubes, cans or bottle caps, and photocuring of polymer coatings, for example of floor or wall coverings based on PVC.

Examples of the photocuring of paper coatings are the colourless varnishing of labels, record sleeves and book covers.

Also of interest is the use of the novel compounds for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP-A-7086. Examples of such compositions are gel coat resins, which are subject to stringent requirements regarding curing activity and yellowing resistance, and fibre-reinforced mouldings, such as, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe" [glass fibre-reinforced plastics], page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of waveguide and optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated through a photomask with UV or visible light, and the unexposed areas of the layer are removed by treatment with a solvent (=developer). Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce printed electronic circuits and photoresists.

The photosensitivity of the novel compositions extends in general from about 200 nm through the UV region into the infrared region (about 20000 nm, in particular 1200 nm) and therefore spans a very broad range. Suitable radiation is present, for example, in sunlight or light from artificial light forces. Consequently, a large number of very different types of light source are employed. Both point sources and arrays ("clamp carpets") are suitable. Examples are carbon arc lamps, xenon arc lamps, medium-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, elecron beams and X-rays, produced by means of synchrotrons or laser plasma. The distance between the lamp and the substrate to be exposed in accordance with the invention may vary depending on the intended application and the type and output of lamp, and may be, for example, from 2 cm to 150 cm. Laser light sources, for example excimer lasers, are especially suitable. Lasers in the visible region or in the IR range can also be employed. In this case, the high sensitivity of the novel materials such as krypton F lasers, for exposure at 248 nm is very advantageous. By this method it is possible to produce printed circuits in the electronics industry, lithographic offset printing plates or relief printing plates, and also photographic image recording materials.

The invention therefore also relates to a process for the photopolymerization of nonvolatile monomeric, oligomeric or polymeric compounds containing at least one ethylenically unsaturated double bond, which comprises adding to the abovementioned compounds at least one compound of the formula I, I' or Ia in which G is a metal from group I of the Periodic Table in the first oxidation state, especially $Na^+$, $K^+$ or $Li^+$, or G is $MgZ^+$ or $CaZ^+$ in which Z is a halogen or $C_1$–$C_4$alkoxy, or G is an ammonium salt, sulfonium salt or phosphonium salt, and irradiating this mixture with light from the infrared range through the UV range to a wavelength of 200 nm.

The invention additionally provides for the use of the above-described composition for production pigmented and unpigmented coating materials, powder coatings, printing inks, printing plates, adhesives, dental compositions, waveguides, optical switches, colour proofing systems, glass fibre cable coatings, screen printing stencils, resist materials, for encapsulating electrical and electronic components, for producing composite compositions, for producing magnetic recording materials, for producing three-dimensional objects by means of stereolithography, for photographical reproductions, and as image recording material, especially for holographic recordings.

The invention additionally provides a coated substrate which is coated on at least one surface with a composition as described above, and describes a process for the photographic production of relief images, in which a coated substrate is subjected to imagewise exposure and then the unexposed portions are removed with a solvent. Of particular interest in this context is the laser beam exposure already mentioned above.

The compounds of the formulae I, I' and Ia are white powders which are stable in air. As already mentioned above, in the compounds either at least two of the radicals $R_1$, $R_2$ and $R_3$ are aromatic hydrocarbon radicals or phenyl radicals substituted in both ortho-positions, or at least one radical $R_1$, $R_2$ or $R_3$ is a sterically bulky aryl radical and the remaining radicals of $R_1$, $R_2$ and $R_3$ are aromatic hydrocarbon radicals or phenyl radicals which are substituted in at least one ortho-position.

These compounds, surprisingly, display good reactivity as unimolecular free-radical photoinitiators; in other words they are sufficiently reactive, even without the addition of coinitiators, to initiate the photopolymerization of ethylenically unsaturated compounds. Those compounds of the formula I, I' and Ia which contain electron-attracting groups are also, in general, acid-stable and can be employed in acidic photopolymerizable formulations as photohardeners.

The novel borate compounds can be employed not only as initiators for photopolymerization reactions, but also as thermal polymerization initiators.

The invention therefore additionally provides for the use of the compounds of the formulae I and I' as initiators for the thermal polymerization of compounds containing ethylenically unsaturated double bonds, and a process for the thermal polymerization of compounds containing ethylenically unsaturated double bonds, which comprises employing as polymerization initiator at least one compound of the formula I or I'.

The examples which follow illustrate the invention in more detail. Parts and percentages are by weight unless stated otherwise, both here and in the remainder of the description and in the claims.

1. PREPARATION OF THE BORANES

EXAMPLE 1: (Method A)

General Procedure for Preparing Aryldimesitylboranes

Preparation of Dimesitylbiphenylborane 1.1 equivalents of butyllithium (0.077 mol) in hexane are added over the course of 15 minutes at −78° C. to a solution of 16.3 g (0.07 mol) of 4-bromobiphenyl in 100 ml of tetrahydrofuran (THF). The reaction mixture is stirred at temperature for 3 h. Then 18.8 g (0.07 mol) of solid dimesitylfluoroborane are added, and the mixture is allowed to warm to room temperature and is stirred for one hour more. The mixture is poured into 500 ml of water and is subjected to extraction with ethyl acetate. Drying over $MgSO_4$, filtration and concentration give a pale yellow solid product which is purified with boiling acetonitrile. 22.9 g (81% of theory) of the product are obtained as a white solid with a melting range of 165–166° C. The shifts δ in the ¹H-NMR are given in Table 1.

EXAMPLES 2–13, 22, 23 and 24:

The boranes 2–13, 22, 23 and 24 are obtained by working in analogy to the method A described above using the corresponding starting materials. The compounds and their structures are shown in Table 1.

TABLE 1

| Ex. | $R_1$ | $R_2$ | $R_3$ | Melting point [° C.] | ¹H-NMR 300 MHz; $CDCl_3$; δ ppm |
|---|---|---|---|---|---|
| 1 | Mesityl | Mesityl | Biphenyl | 165–166 | 7.67(d, 2, J=7Hz) 7.58(s, 4) 7.43(t, 2, J=7Hz) 7.34(t, 1, J=7Hz) 6.83(s, 4) 2.30(s, 6) 2.04(s, 12) |
| 2 | Mesityl | Mesityl | 1-Naphthyl | 170–171 | 7.98(d, 1, J=8Hz) 7.89(d, 2, J=9Hz) 7.56(dd, 1, J=7Hz) 7.51–7.44(m, 2) 7.33–7.27(m, 1) 6.85(s, 4) 2.36(s, 6) 2.00(br s, 12) |
| 3 | Chloro-mesityl | Chloro-mesityl | 1-Naphthyl | 100–104 | 7.94(d, 1 J=8Hz) 7.84(d, 1, J=8.5Hz) 7.76(d, 1, J=8.5Hz) 7.45–7.38(m, 3) 7.25(t, 1, J=~9Hz) 6.89(br s, 1) 6.87(br s, 1) 2.38(s, 6) 2.15–1.80(br m, 12) |
| 4 | Mesityl | Mesityl | 2-Naphthyl | 190–194 | 8.06(s, 1) 7.83(d, 2, J=8Hz) 7.77(d, 1, J=8Hz) 7.58(d, 1, J=8Hz) 7.52(t, 1, J=7Hz) 7.44(t, 1, J=7.5Hz) 6.84(s, 4) 2.26(s, 6) 2.10(s, 12) |
| 5 | o-Tolyl | o-Tolyl | 9-Anthracyl | 132–133 | 8.45(s, 1) 7.99(d, 2, J=8.4Hz) 7.70(d, 2, J=8.5Hz) 7.40–7.25(m, 6) 7.25–7.09(m, 6) 2.07(s, 6) |
| 7 | Chloro-mesityl | Chloro-mesityl | 9-Phenanthryl | 174–177 | 8.75–8.67(m, 2) 7.85–7.79(m, 2) 7.76(s, 1) 7.70(t, 1, J=7Hz) 7.62–7.53(m, 2) 7.34(t, 1, J=7Hz) 6.90(s, 2) 2.39(s, 6) 2.27–1.80(br s, 12) |
| 8 | Dichloro-mesityl | Dichloro-mesityl | 9-Phenanthryl | 210–215 | 8.75–8.65(m, 2) 7.83(d, 1, J=8Hz) 7.77–7.70(m, 3) 7.64–7.56(m, 2) 7.36(t, 1, J=7Hz) 2.59(s, 6) 2.00(s, 12) |
| 9 | Mesityl | Mesityl | 1-Pyrenyl | * | 8.16–7.79(m, 9) 6.81(s, 4) 2.32(s, 6) 1.94(br s, 12) |
| 10 | Chloro- | Chloro- | 1-Pyrenyl | 160–170 | 8.10–7.73(m, 9) |

TABLE 1-continued

| Ex. | R$_1$ | R$_2$ | R$_3$ | Melting point [° C.] | $^1$H-NMR 300 MHz; CDCl$_3$; δ ppm |
|---|---|---|---|---|---|
| | mesityl | mesityl | | | 6.85(br s, 1)<br>6.82(br s, 1)<br>2.32(s, 6)<br>2.10–1.70(2 br s, 12) |
| 11 | Dichloro-mesityl | Dichloro-mesityl | Biphenyl | 161–165 | 7.65–7.59(m, 4)<br>7.50–7.35(m, 5)<br>2.59(s, 6)<br>2.14(s, 12) |
| 12 | Mesityl | Mesityl | p-Bromobiphenyl | 148–150 | 7.59–7.48(m, 8)<br>6.83(s, 4)<br>2.31(s, 6)<br>2.03(s, 12) |
| 13 | Dichloro-phenyl | Dichloro-phenyl | p-Bromodiphenyl | * | 7.60–7.47(m, 8)<br>2.59(s, 6)<br>2.13(s, 12) |
| 22 | Mesityl | Mesityl | p-Fluorophenyl | 119–120 | 7.52(dd, 2 J=8.5 5.5)<br>7.2(t, 2, J32 8.5)<br>6.81(s, 4)<br>2.30(s, 6)<br>1.99(s, 12) |
| 23 | Mesityl | Mesityl | p-Chlorophenyl | 180–181 | 7.44(d, 2, J=8)<br>7.31(d, 2, J=8)<br>6.82(s, 4)<br>2.30(s, 6)<br>1.99(s, 12) |
| 24 | Mesityl | o-Tolyl | o-Tolyl | 128–129 | 7.22(dt, 1, J=7)<br>7.14–7.01(m, 3)<br>6.70(s, 4)<br>2.25(s, 6)<br>2.01(s, 3)<br>1.90(s, 12). |

*not determined

EXAMPLE 14: (Method B)
Preparation of Bis(2-methylnaphth-1-yl)phenylborane 27 ml of a 1.5 M solution of t-butyllithium in pentane are added over the course of 1.5 hours at −78° C. to a solution of 4.42 g (0.02 mol) of 1-bromo-2-methylnaphthalene in 40 ml of THF. The reaction mixture is stirred for 1 hour. 1.1 ml of phenyldifluoroborane (1.26 g, 0.01 mol) are added. The mixture is then allowed to warm to room temperature and is stirred for 2 hours more. The mixture is poured into 300 ml of water and the resulting suspension is filtered. The product is purified by chromatography (SiO$_2$, hexane), to give 1.43 g (i.e. 39% of theory) of the borane as a white solid with a melting point of 208–209° C. The $^1$H-NMR shifts δ measured in CDCl$_3$ are: 7.72 ppm (d,4,J=8.3 Hz), 7.53 ppm (d,2,J=8.6 Hz), 7.40–7.35 ppm (m,3), 7.25–7.15 ppm (m,6), 7.03 ppm (t,2,J=7 Hz) and 2.16 ppm (s,6).

EXAMPLES 15 and 16

The boranes 15–16 are obtained by working in analogy to the methods A or B described above using the corresponding starting materials. The compounds and their structures are shown in Table 2.

TABLE 2

| Ex. | R$_1$ | R$_2$ | R$_3$ | Method | Melting point. [° C.] | $^1$H-NMR 300 MHz; CDCl$_3$; δ ppm |
|---|---|---|---|---|---|---|
| 15 | 9-Anthracyl | 9-Anthracyl | Phenyl | B | <230 | 8.49(s, 2)<br>7.91(t, 8, J=7.6 Hz)<br>7.42–7.25(m, 7)<br>7.17(t, 2, J=4 Hz)<br>7.12–6.98(m, 4) |

TABLE 2-continued

| Ex. | R₁ | R₂ | R₃ | Method | Melting point. [° C.] | ¹H-NMR 300 MHz; CDCl₃; δ ppm |
|---|---|---|---|---|---|---|
| 16 | Mesityl | Mesityl | 4-Phenylthio-phenyl | A | 51–52 | 7.42–7.37(m, 6) 7.06–7.03(m, 2) 6.72(s, 4) 2.21(s, 6) 1.92(s, 12) |

*not determined

EXAMPLE 17

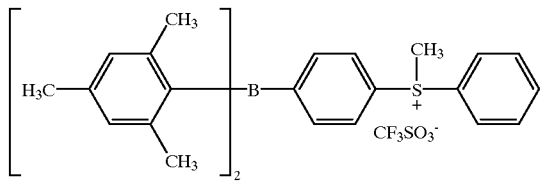

A solution of 1.09 g (0.0025 mol) of (phenylthio) phenyldimesitylborane and 0.45 g (0.00275 mol) of trifluoromethylsulphonate in 5 ml of CH₂Cl₂ is prepared and is left to stand for 21 hours. The reaction mixture is subsequently concentrated and the resulting solid is treated with hexane. Filtration of the white suspension gives 0.94 g (i.e. 63% of theory) of a white solid. The ¹H-NMR shifts δ measured in CD₃COCD₃ are 8.20–8.15 ppm (m,4), 7.87–7.64 ppm (m,5), 6.85 ppm (s,4), 4.00 ppm (s,3), 2.26 ppm (s,6) and 1.94 ppm (s,12).

EXAMPLE 18

(1-dimethylaminonaphthyl)(dimesityl)borane

The compound is prepared by method A described in Example 1 using the corresponding starting materials. The melting point is 160–162° C. The signals in the ¹H-NMR spectrum, measured in CDCl₃, appear at 6.09 ppm (d,1,J=8 Hz); 7.78 ppm (d,1,J=8 Hz); 7.37–7.28 ppm (m,2); 7.11 ppm (dt,1,J=7 Hz); 6.81 (d,1,J=8 Hz); 6.69 ppm (s,4); 2.28 ppm (s,6);2.21 ppm (s,6) and 1.88 ppm (br s,12).

II. PREPARATION OF THE BORATES

EXAMPLE 1a: (Method C)

General Procedure for Preparing Borates from Triorganylboranes

Preparation of tetramethylammonium dimesityl butyl biphenyl borate 1 equivalent of butyllithium (0.005 mol) in hexane is added at 0° C. to a suspension of 2.0 g (0.005 mol) of dimesitylbiphenylborane in 10 ml of diethyl ether at a rate such that the temperature does not exceed 5° C. The reaction mixture is allowed to warm to room temperature and is stirred for 2 h. The resulting two-phase mixture is poured into a vigorously stirred solution of 1.1 g (0.01 mol) of tetramethylammonium chloride in 50 ml of water and 40 ml of hexane. The precipitated solid is filtered off, washed with hexane and water and dried in vacuo to give 2.2 g (82% of theory) of the product as a white solid with a melting range of 141–144° C. In ¹¹B-NMR (measured in CD₃OCD₃), the shift signal δ appears at –8.45 ppm.

EXAMPLES 1a–15a, 25a

The borates of Examples 1a, 2a–2d, 3a–3d, 4a, 4b, 5a, 5b, 6a, 6b, 7a, 8a, 9a, 11a, 14a, 15a and 25a are prepared in accordance with method C indicated above, using the corresponding boranes. Structures, preparation method and physical data are listed in Table 3.

TABLE 3

$$\left[ R_4 - \underset{\underset{R_3}{|}}{\overset{\overset{R_1}{|}}{B}} - R_2 \right]^- G^+$$

| Ex. | R₁ | R₂ | R₃ | R₄ | G⁺ | Melting point. [° C.] | ¹¹B-NMR |
|---|---|---|---|---|---|---|---|
| 1a | Mesityl | Mesityl | Biphenyl | Butyl | N(CH₃)₄ | 141–144 | –8.45 |
| 2a | Mesityl | Mesityl | 1-Naphthyl | Methyl | N(CH₃)₄ | 226–227 | |
| 2b | Mesityl | Mesityl | 1-Naphthyl | Butyl | N(CH₃)₄ | 200–201 | –7.43 |
| 2c | Mesityl | Mesityl | 1-Naphthyl | Butyl | QTX* | 139–148 | –7.52 |
| 2d | Mesityl | Mesityl | 1-Naphthyl | Butyl | Cyanine** | 95–102 | –7.18 |
| 2e*² | Mesityl | Mesityl | 1-Naphthyl | Methyl | Safranin O cation | >230 | –4.65 |
| 2f*³ | Mesityl | Mesityl | 1-Naphthyl | Methyl | N(C₁₀H₂₁)₄ | 104–105 | –9.79 |
| 3a | Chloro-mesityl | Chloro-mesityl | 1-Naphthyl | Methyl | N(CH₃)₄ | 228–233 | –8.08 |
| 3b | Chloro-mesityl | Chloro-mesityl | 1-Naphthyl | Butyl | N(CH₃)₄ | 108–113 | –6.11 |
| 3c | Chloro-mesityl | Chloro-mesityl | 1-Naphthyl | Butyl | QTX* | 139–145 | –6.47 |

TABLE 3-continued $$\left[ \begin{array}{c} R_1 \\ R_4-B-R_2 \\ R_3 \end{array} \right]^- G^+$$

| Ex. | R₁ | R₂ | R₃ | R₄ | G⁺ | Melting point. [° C.] | ¹¹B-NMR |
|---|---|---|---|---|---|---|---|
| 3d | Chloro-mesityl | Chloro-mesityl | 1-Naphthyl | Butyl | Cyanine** | 88–100 | −6.81 |
| 4a | Mesityl | Mesityl | 2-Naphthyl | Methyl | N(CH₃)₄ | 235–238 | −9.77 |
| 4b | Mesityl | Mesityl | 2-Naphthyl | Butyl | N(CH₃)₄ | 208–210 | −8.55 |
| 5a | o-Tolyl | o-Tolyl | 9-Anthracyl | Methyl | N(CH₃)₄ | 220–222 | −8.20 |
| 5b | o-Tolyl | o-Tolyl | 9-Anthracyl | Butyl | N(CH₃)₄ | 170–190 | −7.52 |
| 6a*¹ | Mesityl | Mesityl | 9-Phenanthryl | Butyl | N(CH₃)₄ | 139–140 | |
| 6b | Mesityl | Mesityl | 9-Phenanthryl | Phenyl | N(CH₃)₄ | | −5.03 |
| 7a | Chloro-mesityl | Chloro-mesityl | 9-Phenanthryl | Butyl | N(CH₃)₄ | 150–156 | −5.96 |
| 8a | Dichloro-mesityl | Dichloro-mesityl | 9-Phenanthryl | Butyl | N(CH₃)₄ | 165–170 | −4.79 |
| 9a | Mesityl | Mesityl | 1-Pyrenyl | Butyl | N(CH₃)₄ | 214–215 | −6.76 |
| 10a | Chloro-mesityl | Chloro-mesityl | 1-Pyrenyl | Butyl | N(CH₃)₄ | 146–148 | ++ |
| 11a | Dichloro-mesityl | Dichloro-mesityl | Biphenyl | Methyl | N(CH₃)₄ | 203–205 | −7.96 |
| 13a | Dichloro-mesityl | Dichloro-mesityl | 4'-Bromobiphenyl | Methyl | N(CH₃)₄ | ++ | ++ |
| 14a | 2-Methyl-naphth-1-yl | 2-Methyl-naphth-1-yl | Phenyl | Butyl | N(CH₃)₄ | 200–202 | −7.97 |
| 15a | 9-Anthracyl | 9-Anthracyl | Phenyl | Butyl | N(CH₃)₄ | 165–168 | −6.89 |
| 16a | Mesityl | Mesityl | (4-Phenylthio)phenyl | Methyl | N(CH₃)₄ | 185–186 | −5.35 |
| 18a | Mesityl | Mesityl | 1-Dimethylaminonaphthyl | Methyl | N(CH₃)₄ | 145–148 | −4.74 |
| 25a*⁴ | Chloro-mesityl | Chloro mesityl | p-(thiophen-yl)-phenyl | methyl | triphenyl-sulfonium | 110–111 | −4.46 |

*QTX is

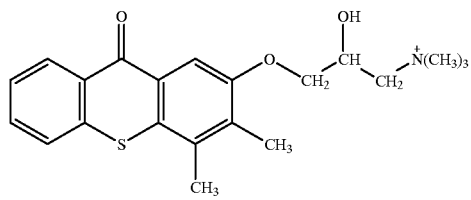

**Cyanine is

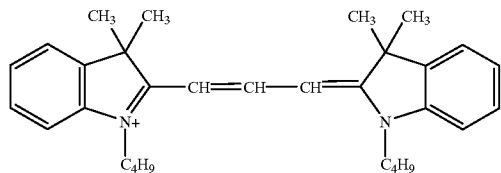

*¹the preparation of the corresponding borane is described in CA-A-912019
*²prepared using Safranin O (chloride)
*³prepared using tetradecylammonium bromide
*⁴the corresponding borane educt is prepared according to method A
++ the ¹H-NMR shifts are given in Table 3a

TABLE 3a

| Example | $^1$H-NMR shifts δ [ppm], coupling constant J [Hz] |
|---|---|
| 10a | 8.45(br m, 1); 8.01–7.71(m, 8); 6.80–6.59(m, 2); 3.01(s, 12); 2.25(s, 6); 1.90–1.60(br m, 12); 1.27(br m, 4); 1.06(br m, 2); 0.77(br t, 3), measured in CD$_3$CN |
| 13a | 7.66(s, 4); 7.66(br m, 4); 3.17(s, 12); 2.54(s, 6); 2.06(s, 12); 0.50(br s, 3), measured in CD$_3$COCD$_3$ |

EXAMPLE 17a

Methyl 4-[(phenyl)(methyl)sulfonio]phenyl dimesityl borate Compound of the formula I', in which R$_2$ =mesityl, R$_3$=mesityl, R$_4$=methyl,

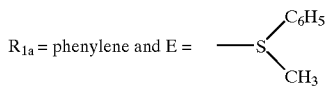

The compound is prepared by method C starting from compound 17, but is worked up by concentration, subsequent dissolution in ethyl acetate, washing with water, drying over magnesium sulphate, filtration and renewed concentration. A white solid with a melting point of 195–200° C. is obtained. The shift in the $^{11}$B-NMR spectrum is at –5.75 ppm, measured in DMSO-d$_6$.

EXAMPLE 19a

Methyl 1-trimethylammonionaphthyl dimesityl borate Compound of the formula I', in which R$_2$=mesityl, R$_3$=mesityl, R$_4$=methyl, R$_{1a}$=naphthylene and E=N(CH$_3$)$_3$ This compound is obtained starting from compound 18a using the method described for compound 17 but, after concentration of the reaction mixture, dissolving the residue in ethyl acetate and washing it with water. Treatment with MgSO$_4$, filtration and concentration give a white solid. The shifts δ in the $^1$H-NMR spectrum (CD$_3$COCD$_3$) appear at 8.63 ppm (d,1,J=9 Hz); 8.28 ppm (d,1,J=8 Hz); 7.61 ppm (m,1); 7.55 ppm (d,1,J=8 Hz); (m,2); 6.62 ppm (s,4) 3.90 ppm (s,9); 2.27 ppm (s,6); 1.83 ppm (s,12); 0.66 ppm (m,3).

EXAMPLE 20a

Methyl 1-benzyldimethylammonionaphthyl dimesityl borate Compound of formula I', in which R$_2$=mesityl, R$_3$=mesityl, R$_4$=methyl, R$_{1a}$=naphthylene and E=N(CH$_3$)$_2$(CH$_2$C$_6$H$_5$)

This compound is obtained starting from compound 18a and using the method described for compound 17 but carrying out the reaction with two equivalents of benzyl bromide in acetonitrile and, after concentration of the reaction mixture, dissolving the residue in ethyl acetate and washing it with water. Treatment with MgSO$_4$, filtration and concentration give a white solid having a melting point of 125–128° C. The shifts δ [ppm] in the $^1$H-NMR spectrum (CD$_3$CN) appear at 8.62 (d,1,J=9 Hz); 8.42 (d,1,J=9 Hz); 7.64 (t,1,J=7 Hz); 7.47–7.00 (m,6); 6.83 (d,2,J=7 Hz); 6.61 (s,4); 5.44 (s,2); 3.83 (s,6); 2.26 (s,6), 1.84 (s,12); 0.69 (m,3).

EXAMPLE 21 a

Tetramethylammonium 2,2'-biphenylyl Dimesityl Borate

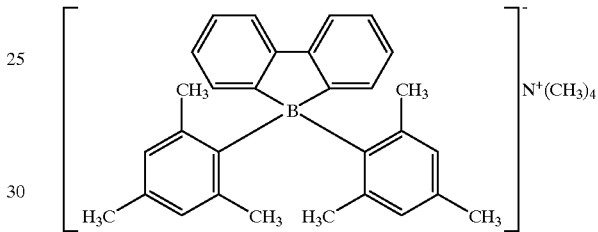

60.5 ml of a 1.5 M solution of t-butyllithium in pentane (0.091 mol) are added over the course of 2.5 hours at –78° C. to a stirred solution of 7.06 g (0.023 mol) of 2,2'-dibromobiphenyl in 80 ml of tetrahydrofuran (THF). The reaction mixture is subsequently stirred at –78° C for one hour more, and then 6.06 g (0.0226 mol) of solid dimesitylfluoroborane are added. The reaction mixture is allowed to warm slowly to room temperature and is stirred at this temperature for 15 hours more. The solvent is removed and the resulting solid is dissolved in 100 ml of 4:1 methanol:H$_2$O. The suspension is filtered and the filtrate is treated with 2.97 9 (0.027 mol) of tetramethylammonium chloride.

The precipitated solid is filtered off, washed with ethyl acetate and dried in vacuo to give 6.31 g (59%) of a white solid whose melting point is more than 230° C. The shift signal in the $^{11}$B-NMR spectrum, recorded in CD$_3$CN, is at –1.02 ppm.

EXAMPLES 2g–2t

The compounds of Example 2g–2t are prepared by method C. Structures and data are presented in Table 3b.

TABLE 3b

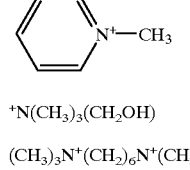

| Example | Cation | Melting point [° C.] | $^{11}$B-NMR; δ [ppm] |
|---|---|---|---|
| 2g | $^+$N(CH$_3$)$_3$(n-C$_{16}$H$_{33}$) | 70–72 | −4.65 (Acetone-d$_6$) |
| 2h | 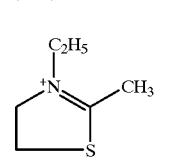 | ++ | −8.83 (CDCl$_3$) |
| 2i | 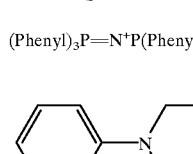 | 135–138 | −4.65 (Acetone-d$_6$) |
| 2j | $^+$N(CH$_3$)$_3$(CH$_2$OH) | 161–163 | −4.66 (Acetone-d$_6$) |
| 2k | (CH$_3$)$_3$N$^+$(CH$_2$)$_6$N$^+$(CH$_3$)$_3$ | 227–229 | −4.67 (Acetone-d$_6$) |
| 2l | $^+$N(C$_2$H$_5$)$_3$([CH$_2$]$_3$Br) | 120–121 | −4.66 (Acetone-d$_6$) |
| 2m | (CH$_3$)$_3$—N$^+$—CH$_2$—CH—CH$_2$ (epoxide) | 130–138 | −4.66 (Acetone-d$_6$) |
| 2n | 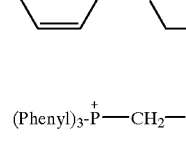 | 150–152 | −4.65 (Acetone-d$_6$) |
| 2o | (Phenyl)$_3$P═N$^+$P(Phenyl)$_3$ | 181–185 | −4.65 (Acetone-d$_6$) |
| 2p | 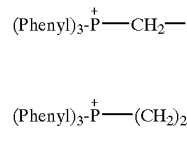 | 183–186 | −4.65 (Acetone-d$_6$) |
| 2q | (Phenyl)$_3$-P$^+$—CH$_2$—C(═O)—OCH$_3$ | 130–131 | −9.81 (Acetone-d$_6$) |
| 2r | (Phenyl)$_3$-P$^+$—CH$_2$—CH═CH$_2$ | 98–110 | −9.81 (CDCl$_3$) |
| 2s | (Phenyl)$_3$-P$^+$—(CH$_2$)$_2$-(1,3-dioxane) | 103–108 | −4.65 (Acetone-d$_6$) |
| 2t | (Phenyl)$_3$S$^+$ | 127–135 | −4.66 (Acetone-d$_6$) |

++ not determined

EXAMPLES 22a, 22b, 23a, 23b AND 24a

The compounds are obtained in accordance with method C described above using the corresponding starting materials. The compounds are indicated in Table 4.

TABLE 4

$$\left[ \begin{array}{c} R_1 \\ | \\ R_4 \text{---} B \text{---} R_2 \\ | \\ R_3 \end{array} \right]^{-} X^{+}$$

| Ex. | $R_1$ | $R_2$ | $R_3$ | $R_4$ | $X^+$ | Melting point [° C.] | $^{11}$B-NMR |
|---|---|---|---|---|---|---|---|
| 22a | Mesityl | Mesityl | p-Fluoro-phenyl | Methyl | $N(CH_3)_4$ | 258–260 | −9.86 |
| 22b | Mesityl | Mesityl | p-Fluoro-phenyl | Butyl | $N(CH_3)_4$ | 221–225 | −8.63 |
| 23a | Mesityl | Mesityl | p-Chloro-phenyl | Methyl | $N(CH_3)_4$ | 255–256 | −9.96 |
| 23b | Mesityl | Mesityl | p-Chloro-phenyl | Butyl | $N(CH_3)_4$ | 247–249 | −8.73 |
| 24a | Mesityl | Mesityl | o-Tolyl | Methyl | $N(CH_3)_4$ | >230 | ++ |

++ not determined

EXAMPLE 26

Reactivity Test in a Clearcoat

A photocurable composition is prepared by mixing the following components:

10.0 g of dipentaerythritol Monohydroxypentaacrylate, ®SR399, Sartomer (Craynor, France 15.0 g of tripropylene glycol diacrylate 15.0 g of N-vinylpyrrolidone, Fluka 10.0 g of trismethylolpropane triacrylate, Degussa 50.0 g of urethane acrylate ®Actilan AJ20, SociétéNationale des Poudres et Explosifs 0.3 g of levelling assistant ®Byk 300, Byk-Mallinckrodt.

Portions of this composition are heated to 40° C., and 1.6% of the borate photoinitiator to be tested, based on the total quantity of the formulation, are dissolved in the formulation at this temperature. All operations are carried out under red light. The samples to which initiator has been added are applied to a 300 μm aluminium foil. The thickness of the dry film is about 60–70 μm. A 76 μm polyester film is applied to the film and a standardized test negative with 21 steps of different optical density (Stouffer wedge) is placed thereon. The sample is covered with a second UV-transparent film and is compressed on a metal plate by means of reduced pressure. Exposure is carried out for 20 seconds using a 5 kW MO61 lamp at a distance of 30 cm. Following exposure, the cover films and the mask are removed and the exposed film is developed in ethanol at 23° C. in an ultrasound bath for 10 seconds. It is dried at 40° C. in a convection oven for 5 minutes. The sensitivity of the initiator system used is characterized by indicating the last wedge step reproduced without tack. The higher the number of steps, the more sensitive the system tested. The results are compiled in Tables 4a to 4g.

TABLE 4a

| Compound | Number of steps cured |
|---|---|
| 1a | 11 |
| 6a | 12 |

TABLE 4b

| Compound | Number of steps cured |
|---|---|
| 2a | 3 |
| 4b | 5 |
| 4a | 6 |

TABLE 4c

| Compound | Number of steps cured |
|---|---|
| 2b | 8 |
| 3b | 7 |
| 7a | 10 |
| 8a | 10 |
| 9a | 13 |

TABLE 4d

| Compound | Number of steps cured |
|---|---|
| 14a | 9 |

TABLE 4e

| Compound | Number of steps cured |
|---|---|
| 11a | 6 |

TABLE 4f

| Compound | Number of steps cured |
|---|---|
| 13a | 8 |
| 16a | 6 |

TABLE 4f-continued

| Compound | Number of steps cured |
| --- | --- |
| 19a | 7 |
| 20a | 10 |

TABLE 4g

| Compound | Number of steps cured |
| --- | --- |
| 22b | 6 |

EXAMPLE 27

0.4% of the borate photoinitiator to be tested and 0.3% of (N,N'-dibutyl)dimethylindocarbocyanine chloride are incorporated into a formulation as described in Example 25. Film preparation, curing and the determination of the reactivity are carried out likewise as described in Example 26. The results are reproduced in Tables 5 to 5f.

TABLE 5

| Compound | Number of steps cured | Bleaching behaviour* |
| --- | --- | --- |
| 1a | 19 | b |
| 6a | 18 | b |

*b = formulation bleaches out (visual examination)

TABLE 5a

| Compound | Number of steps cured | Bleaching behaviour* |
| --- | --- | --- |
| 2a | 18 | b |
| 4b | 20 | b |
| 4a | 17 | — |

*b = formulation bleaches out (visual examination)
— = visually, no bleaching out is found

TABLE 5b

| Compound | Number of steps cured | Bleaching behaviour* |
| --- | --- | --- |
| 2b | 18 | b |
| 3b | 20 | b |
| 7a | 17 | — |
| 8a | 15 | — |
| 9a | 18 | b |

*b = formulation bleaches out (visual examination)
— = visually, no bleaching out is found

TABLE 5c

| Compound | Number of steps cured | Bleaching behaviour* |
| --- | --- | --- |
| 14a | 16 | b |

*b = formulation bleaches out (visual examination)

TABLE 5d

| Compound | Number of steps cured |
| --- | --- |
| 11a | 14 |

TABLE 5e

| Compound | Number of steps cured |
| --- | --- |
| 2f | 15 |

TABLE 5f

| Compound | Number of steps cured | Bleaching behaviour* |
| --- | --- | --- |
| 13a | 11 | — |
| 16a | 14 | — |
| 19a | 9 | — |
| 20a | 12 | b |

*b = formulation bleaches out (visual examination)
— = visually, no bleaching out is found

EXAMPLE 28

Photocuring of a Monomer-polymer Mixture

A photocurable composition is prepared by mixing 37.64 g of ®Sartomer SR 444, pentaerythritol triacrylate, (Sartomer Company, Westchester, USA)

10.76 g of ®Cymel 301, hexamethoxymethylmelamine (American Cyanamid, USA)

47.30 g of ®Carboset 525, thermoplastic polyacrylate containing carboxyl groups (B.F. Goodrich)

4.30 g of polyvinylpyrrolidone PVP (GAF, USA)

319.00 g of methylene chloride and 30.00 g of methanol.

Portions of this composition are mixed with in each case 1.6% of a novel borate, based on the solids content, by stirring at room temperature for one hour. All operations are carried out under red light. The samples to which initiator has been added are applied to a 300 µm aluminium foil (10×15 cm). The solvent is removed first of all by drying at room temperature for 5 minutes followed by heating at 60° C. in a convection oven for 15 minutes. A 76 µm thick polyester film is placed on the approximately 30–35 µm film thus prepared, and a standardized test negative with 21 steps of different optical density (Stouffer wedge) is applied thereto. The sample is covered with a second UV-transparent film and is compressed on a metal plate by means of reduced pressure. The sample is then exposed for 40 seconds using a 4 kW xenon lamp at a distance of 30 cm. Following exposure, the films and the mask are removed and the coated film is developed with a 0.85% strength solution of sodium carbonate in water in an ultrasound bath for 240 seconds. It is then dried at 60° C. in a convection oven for 15 minutes. The sensitivity of the initiator system used is characterized by stating the last wedge step reproduced without tack. The higher the number of steps, the more sensitive the system. In this scale, an increase by two steps denotes approximately a doubling of the curing rate. The results are indicated in Tables 6 and 6a.

TABLE 6

| Compound | Number of steps cured |
| --- | --- |
| 2a | 6 |
| 4a | 5 |
| 4b | 7 |

TABLE 6a

| Compound | Number of steps cured |
|---|---|
| 7a | 10 |
| 8a | 8 |
| 3b | 5 |
| 2b | 9 |
| 14a | 6 |
| 13a | 5 |
| 19a | 5 |
| 20a | 6 |
| 16a | 6 |

EXAMPLE 29

0.3% of a borate photoinitiator with dye cation is incorporated into a formulation as described in Example 28. Film preparation, curing and the determination of the reactivity are likewise carried out as described in Example 28. The results are set out in Tables 7 and 7a.

TABLE 7

| Compound | Number of steps cured |
|---|---|
| 2c | 19 |
| 2d | 10 |

TABLE 7a

| Compound | Number of steps cured | Bleaching behaviour* |
|---|---|---|
| 3c | 10 | — |
| 3d | 18 | b |
| 2e | 16 | — |

*b = formulation bleaches out (visual examination)
— = visually, no bleaching out is found

EXAMPLE 30

A photocurable composition is prepared by mixing 37.64 g of ®Sartomer SR 444, pentaerythritol triacrylate, (Sartomer Company, Westchester, USA)

10.76 g of ®Cymel 301, hexamethoxymethylmelamine (American Cyanamid, USA)

47.30 g of ®Carboset 525, thermoplastic polyacrylate containing carboxyl groups (B.F. Goodrich)

4.30 g of polyvinylpyrrolidone PVP (GAF, USA)

319.00 g of methylene chloride and 30.00 g of methanol.

Portions of this composition are mixed with in each case 0.4% of the borate from Example 2a, 0.4% of isopropylthioxanthone and 0.4% of (4-methylthiobenzoyl)methyl-1-morpholinoethane, based on the solids content, by stirring at room temperature for one hour. All operations are carried out under red light. The samples to which initiator has been added are applied to a 200 μm aluminium foil (10×15 cm). The solvent is removed first of all by drying at room temperature for 5 minutes followed by heating at 60° C. in a convection oven for 15 minutes. A 76 μm thick polyester film is placed on the approximately 30–35 μm film thus prepared, and a standardized test negative with 21 steps of different optical density (Stouffer wedge) is applied thereto. The sample is covered with a second UV-transparent film and is compressed on a metal plate by means of reduced pressure. The sample is then exposed for 40 seconds using an SMX-3000 metal halide-doped high-pressure mercury lamp at a distance of 30 cm. Following exposure, the cover films and the mask are removed and the coated film is developed with a 1% strength solution of sodium carbonate in water in an ultrasound bath for 180 seconds. It is then dried at 60° C. in a convection oven for 15 minutes. The sensitivity of the initiator system used is characterized by stating the last wedge step reproduced without tack. The higher the number of steps, the more sensitive the system. In this scale, an increase by two steps denotes approximately a doubling of the curing rate. The results are indicated in Table 8.

TABLE 8

| Number of steps reproduced after | | |
|---|---|---|
| 10 s | 20 s | 40 s |
| 10 | 12 | 14 |

EXAMPLE 31

0.6% of the borate from Example 2a, 0.4% of isopropylthioxanthone and 1.2% of Cyracure®

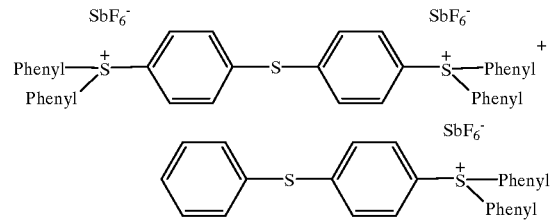

UVI-6974(Union Carbide) = as a 50% strength solution in propylene carbonate, based on the solids content, are incorporated into a composition as described in Example 27. The implementation and evaluation of the tests are carried out likewise as described in Example 27. The results are given in Table 9.

TABLE 9

| Number of steps reproduced after | | |
|---|---|---|
| 10 s | 20 s | 40 s |
| 9 | 12 | 14 |

EXAMPLE 32

0.4% of the borate from Example 2a, 0.4% of isopropylthioxanthone and 0.8% of Cyracure®

TABLE 9

| Number of steps reproduced after | | |
|---|---|---|
| 10 s | 20 s | 40 s |
| 9 | 12 | 14 | as a 50% strength solution in propylene carbonate and 0.4% of (4-methylthiobenzoyl)methyl-1-morpholinoethane, based on the solids content, are incorporated into a composition as described in Example 30. The implementation and evaluation of the tests are carried out likewise as described in Example 30. The results are given in Table 10.

TABLE 10

| Number of steps reproduced after | | |
|---|---|---|
| 10 s | 20 s | 40 s |
| 11 | 13 | 15 |

EXAMPLE 33

0.4% of a borate photoinitiator and 0.3% of the dye safranin O are incorporated into a formulation as described in Example 28. Film preparation, curing and the determination of the reactivity are carried out likewise as described in Example 28. The results are presented in Table 11.

TALBE 11

| Compound | Number of steps cured |
|---|---|
| 2g | 16 |
| 2h | 16 |
| 2i | 3 |
| 2j | 17 |
| 2k | 18 |
| 2m | 17 |
| 2o | 13 |

TALBE 11-continued

| Compound | Number of steps cured |
|---|---|
| 2p | 15 |
| 2q | 15 |
| 2r | 15 |
| 2s | 15 |

EXAMPLE 34

0.4% of the compound 2a and 0.3% of a dye are incorporated into a formulation as described in Example 28. In addition, instead of the xenon lamp, a frequency-doubled Nd/YAG laser (COHERENT DPSS 532-50, beam diameter 0.7 mm, divergence <1.3 mrad) is used with monochromatic light of wavelength 532 nm and an output of 50 mW. The laser beam with a diameter of about 3.3 mm is moved at a rate of 6 mm/s over a 21-step Stouffer wedge which is fixed on the sample. After development, a line varying in width and length remains. For evaluation, a statement is made of the number of steps at which a cured line can still be seen. Film preparation, curing and the determination of the reactivity are likewise as described in Example 28. The results are presented in Table 12.

TABLE 12

| Dye | Number of steps reproduced | Bleaching behaviour* |
|---|---|---|
| 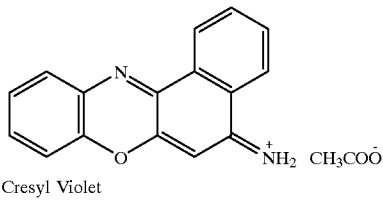 Cresyl Violet | 9 | b |
| 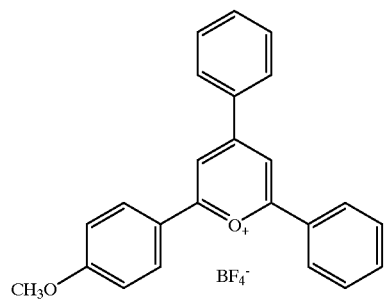 | 7 | — |
| 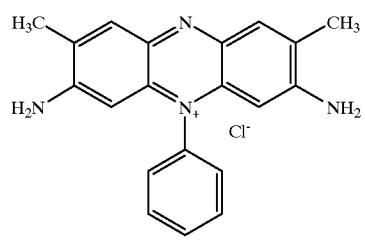 Safranin O | 19 | — |

TABLE 12-continued

| Dye | Number of steps reproduced | Bleaching behaviour* |
|---|---|---|
| Brilliant Green | 15 | — |
| Methylene Blue | 12 | b |
| Pyronine GY | 13 | — |
| Crystal violet | 16 | — |
| [cyanine dye structure] | 21 | b |
| [bis-chromenylium dye structure] | 15 | b |

TABLE 12-continued

| Dye | Number of steps reproduced | Bleaching behaviour* |
|---|---|---|
| 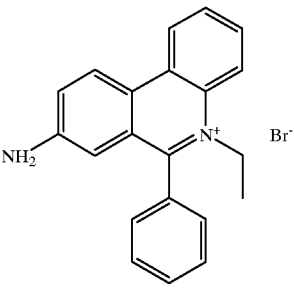  Ethidium bromide | 13 | — |
| 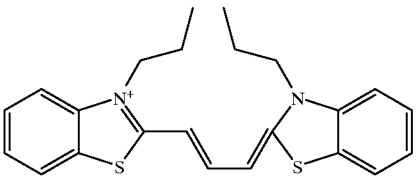 | 17 | b |

*b = formulation bleaches out (visual examination)
— = visually, no bleaching out is found

EXAMPLE 35

The same formulations as in Example 28 are used, and portions of this composition are mixed with 0.4%, based on the total quantity of the formulation, of the compound 5 and 0.3% of a dye. All operations are carried out under red light. The samples are placed in pill bottles with a diameter of about 3 cm. These formulations are subjected in the bottles to exposure with a frequency-doubled Nd/YAG laser (COHERENT DPSS 532-50, beam diameter 0.7 mm, divergence <1.3 mrad) with monochromatic light of wavelength 532 nm at an output of 50 mW for 10 seconds at a distance of 30 cm. Following exposure, the uncured formulation is poured out and the cured layer which remains is developed in ethanol at 23° C. in an ultrasound bath for 10 seconds. Drying takes place at 40° C. in a convection oven for 5 minutes. After development, a needlelike figure varying in length is left standing. Evaluation is made by stating the length of the figure, which is a measure of the capacity for through-curing. The dyes used and the results are reproduced in Table 13:

TABLE 13

| Dye | Length of the figure formed, in mm |
|---|---|
| Safranin O | 3 |
| Rhodamine B | 1 |
| Methylene blue | 12 |

TABLE 13-continued

| Dye | Length of the figure formed, in mm |
|---|---|
| 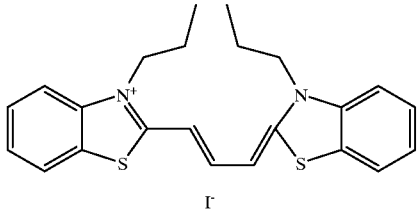 | 5 |
| 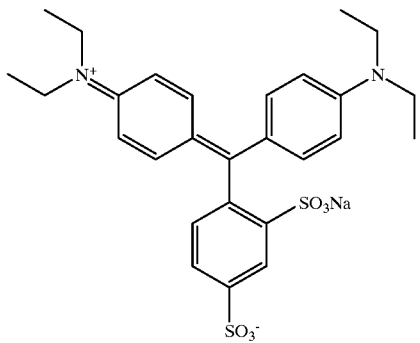  Patent Blue | 10 |

TABLE 13-continued

| Dye | Length of the figure formed, in mm |
|---|---|
| 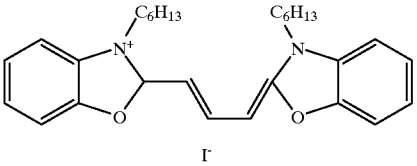 I⁻ | 8 |

EXAMPLE 36

The procedure of Example 28 is repeated but using 0.4% of the dye-borate salts. In addition, instead of the xenon lamp, a frequency-doubled Nd/YAG laser (COHERENT DPSS 532-50, beam diameter 0.7 mm, divergence <1.3 mrad) is used with monochromatic light of wavelength 532 nm and an output of 100 mW. The laser beam with a diameter of about 3.3 mm is moved at a rate of 6 mm/s over a 21-step Stouffer wedge which is fixed on the sample. After development, a line varying in width and length remains. For evaluation, a statement is made of the number of steps at which a cured line can still be seen. The dyes used and results are presented in Table 14.

TABLE 14

| Compound | Number of steps reproduced |
|---|---|
| 2e | 11 |

EXAMPLE 37

The procedure of Example 35 is repeated but using dye-borate salts in concentrations such that the optical density of a 2 mm film is 0.5 for the wavelength of 532 nm, and additional compound 2a is employed. In contrast to Example 34, use is made of a frequency-doubled Nd/YAG laser (COHERENT DPSS 532-100, beam diameter 0.7 mm, divergence <1.3 mrad) with monochromatic light of wavelength 532 nm and an output of 100 mW, and exposure is carried out for 5 seconds at a distance of 30 cm. The results are presented in Table 15.

TABLE 15

| Compound | Concentration of compound 2a | Length of the figure formed, in mm | Bleaching behaviour* |
|---|---|---|---|
| 0.03% 2e | 0 | 5 | — |
| 0.03% 2e | 0.3% | 14 | b |
| 0.03% 2e | 0.6% | 17 | b |

*b = formulation bleaches out (visual examination)
— = visually, no bleaching out is found

EXAMPLE 38

The same formulations as in Example 26 are used, and portions of this composition are mixed with 0.4%, based on the total quantity of the formulation, of the compound 2a and 0.3% of a dye. All operations are carried out under red light. The samples are placed in black plastic lids with a diameter of about 1.5 cm and a height of about 12 mm and are covered with a Mylar film. These samples are exposed to daylight and a dose of 1200 mJ/cm². After exposure, the uncured formulation is poured out and the cured layer which remains is developed in ethanol at 23° C. in an ultrasound bath for 1 minute. Drying takes place at 40° C. in a convection oven for 5 minutes. For evaluation, the thickness of the cured layer is measured, and this is a measure of the capacity for through-curing. The dyes used and the results are reproduced in Table 16:

TABLE 16

| Dye | Thickness of the cured layer, in mm |
|---|---|
| Safranin O | 1.45 |
| Methylene blue | 2.94 |

EXAMPLE 39

The procedure of Example 38 is repeated but using, instead of mixtures of borates and dyes, 0.4% of the novel dye-borate salts and, in addition, compound 2a. The results are reproduced in Table 17:

TABLE 17

| Compound | Concentration of compound 2a | Thickness of the cured layer, in μm |
|---|---|---|
| 2e | 0 | 1140 |
| 2e | 0.3% | 1440 |
| 2e | 0.6% | 1880 |

EXAMPLE 40

The procedure of Example 26 is repeated but adding in each case 0.4% of a cationic photoinitiator together with 0.4% of the compound 2a. The results are described in Table 18.

TABLE 18

| Cationic photoinitator | Number of steps cured |
|---|---|
| [structure: diphenyliodonium with 4-heptyloxyphenyl, SbF$_6^-$ counterion] | 4 |
| [structure: diphenyliodonium with 4-(C$_{10}$H$_{21}$-CH(OH)-CH$_2$-O)phenyl, SbF$_6^-$ counterion] | 4 |
| [structure: bis-triphenylsulfonium thiodiphenyl bis(PF$_6^-$)] | 8 |
| [structure: UVI 6990, sulfonium PF$_6^-$ salt] UVI 6990 | |

EXAMPLE 41

The procedure of Example 26 is repeated but adding in each case 0.4% of a cationic photoinitiator together with 0.4% of the compound 2a and 0.3% of a dye. The results are described in Table 19.

TABLE 19

| Cationic photoinitiator | Dye | Number of steps cured |
|---|---|---|
| Triphenylsulfonium hexafluorophosphate | Methylene blue | 10 |

TABLE 19-continued

| Cationic photoinitiator | Dye | Number of steps cured |
|---|---|---|
| [structure: iodonium SbF6 with phenyl and 4-alkoxyphenyl] | Safranin O | 14 |
| [structure: iodonium SbF6 with phenyl and 4-alkoxyphenyl] | [structure: bis(7-diethylamino-coumarin-3-yl) ketone] | 15 |
| [structure: two triphenylsulfonium PF6 linked via diphenyl sulfide] UVI 6990 | [structure: bis(7-diethylamino-coumarin-3-yl) ketone] | 17 |

EXAMPLE 42

The procedure of Example 26 is replaced but adding in each case 0.4% of the compound 2a and 0.3% of a dye or electron acceptor. The results are described in Table 20.

TABLE 20

| Dyr or electron acceptor | Number of steps cured | Bleaching behaviour |
|---|---|---|
| [structure: bis(7-diethylamino-coumarin-3-yl) ketone] | 14 | b |

TABLE 20-continued
| Dyr or electron acceptor | Number of steps cured | Bleaching behaviour |
|---|---|---|
| 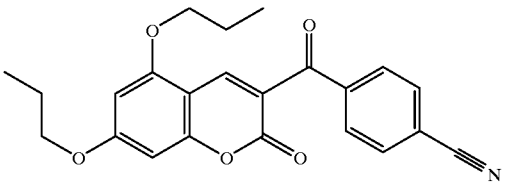 | 10 | b |
| 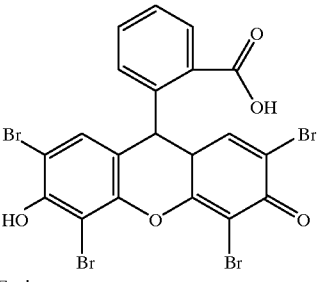<br>Eosine | 12 | — |
| Quantacure ITX | 11 | — |
| CG 26-0753<br>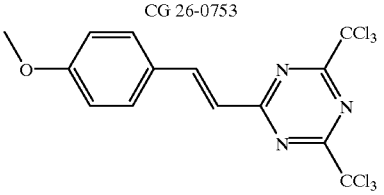 | 12 | b |
| 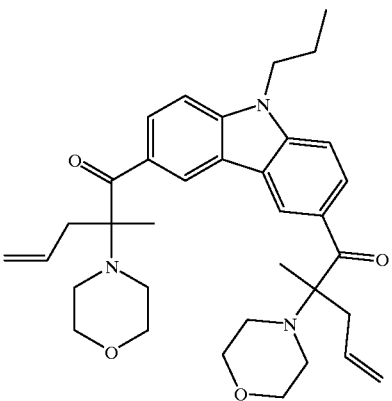 | 12 | — |
*b = formulation bleaches out (visual examination)
— = visually, no bleaching out is found

EXAMPLE 43

The procedure of Example 26 is repeated but adding in each case 2% of the compound 2a and 2% of an electron acceptor. The results are described in Table 21.

TABLE 21

| Dye or electron acceptor | Number of steps cured |
|---|---|
| 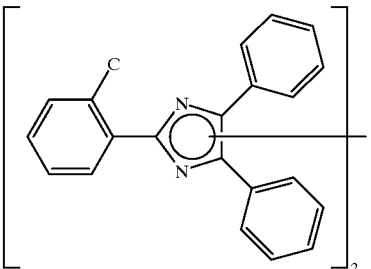<br>o-Chlorohexaarylbisimidazole | 4 |

EXAMPLE 44

The procedure of Example 26 is repeated but adding in each case 0.4% of the compound 2a and 0.3% of an electron acceptor and 0.3% of a dye. The results are described in Table 22.

TABLE 22

| Electron acceptor | Dye | Number of steps cured |
|---|---|---|
| Quantacure ITX | Safranin O | 13 |

What is claimed is:

1. A process for the photopolymerization of nonvolatile monomeric, oligomeric or polymeric compounds containing at least one ethylenically unsaturated double bond, which comprises adding to the abovementioned compounds at least one compound of the formula I, I' or Ia

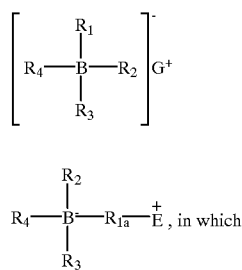

(I)

(I')

$R_1$, $R_2$ and $R_3$ independently of one another are phenyl or another aromatic hydrocarbon, with or without any heteroatoms, which radicals are unsubstituted or are substituted 1–5 times by unsubstituted $C_1$–$C_{20}$alkyl, $OR_6$-substituted $C_1$–$C_{20}$alkyl, $R_7R_8N$-substituted $C_1$–$C_{20}$alkyl, $C_2$–$C_{20}$alkyl which is interrupted by one or more radicals O, $S(O)_p$ or $NR_5$, or the radicals phenyl or another aromatic hydrocarbon are substituted 1–5 times by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$, CN,

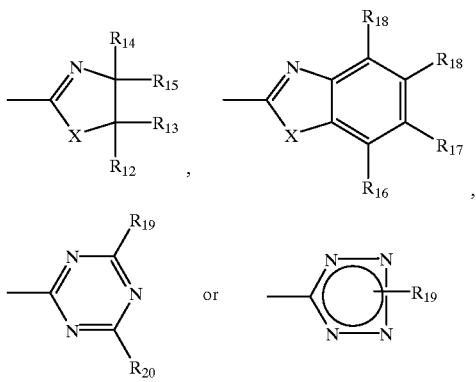

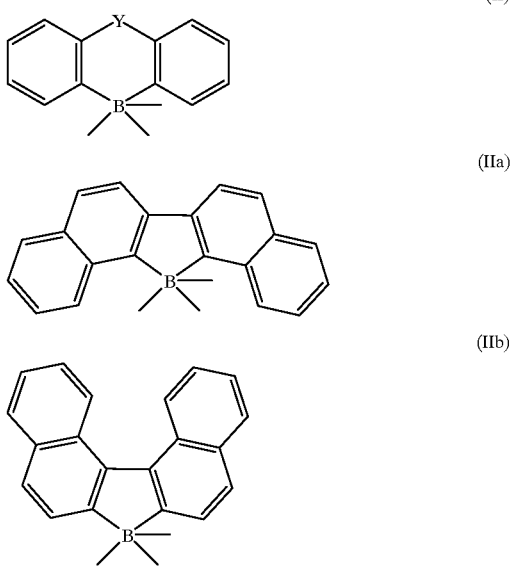

or the radicals $R_2$ and $R_3$ form bridges to produce structures of the formula II, IIa or IIb (II)

(IIa)

(IIb)

whose aromatic rings are unsubstituted or are substituted by $C_1$–$C_{20}$alkyl, $C_2$–$C_{20}$alkyl which is interrupted by one or more radicals O, $S(O)_p$ or $NR_5$, or the aromatic rings are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, halogen, $R_9R_{10}P(O)_q$ or $R_9R_{10}R_{11}Sn$;

with the provisos that not more than two of the radicals $R_1$, $R_2$ and $R_3$ are identical and either at least two of the radicals $R_1$, $R_2$ and $R_3$ are aromatic hydrocarbon radicals or phenyl radicals which are substituted in both ortho-positions, or at least one radical $R_1$, $R_2$ or $R_3$ is a sterically bulky aryl radical and the remaining radicals of $R_1$, $R_2$ and $R_3$ are aromatic hydrocarbon radicals or phenyl radicals which are substituted in at least one ortho-position;

$R_{1a}$ is a divalent aromatic hydrocarbon radical which is unsubsituted or is substituted by $C_1$–$C_6$alkyl, $OR_6$, $S(O)_pR_6$, $OS(O)_2R_6$, $NR_8R_7$, $C(O)OR_6$, $C(O)NR_8R_7$, $C(O)R_9$, $SiR_9R_{10}R_{11}$ or halogen, or $R_{1a}$ is phenyl-$C_1$–$C_6$alkylene;

$R_4$ is phenyl or another aromatic hydrocarbon radical, with or without any heteroatoms, which radicals are unsubstituted or substituted 1–5 times by unsubstituted $C_1$–$C_{20}$alkyl, $OR_6$-substituted $C_1$–$C_{20}$alkyl, $R_7R_8N$-substituted $C_1$–$C_{20}$alkyl, $C_2$–$C_{20}$alkyl which is interrupted by one or more radicals O, $S(O)_p$ or $NR_5$, or the radicals phenyl or another aromatic hydrocarbon are substituted 1–5 times by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$, CN,

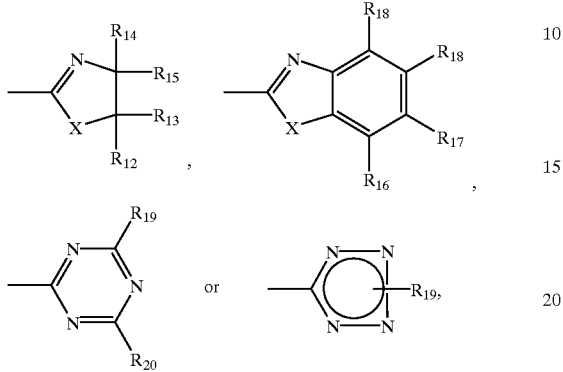

or $R_4$ is $C_1$–$C_{20}$alkyl, $C_2$–$C_{20}$alkyl which is interrupted by one or more radicals O, $S(O)_p$ or $NR_5$, or $R_4$ is $C_3$–$C_{12}$cycloalkyl, $C_2$–$C_8$alkenyl, phenyl-$C_1$–$C_6$alkyl or naphthyl-$C_1$–$C_3$alkyl where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsubstituted or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$ or CN;

Y is $(CH_2)_n$, CH=CH, C(O), $NR_5$, O, $S(O)_p$ or

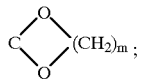

n is 0, 1 or 2;
m is 2 or 3;
p is 0, 1 or 2;
q is 0 or 1;
E is $R_{21}R_{22}R_{23}P$, $R_7R_{7a}R_8N$ or $R_6R_{6a}S$;
$R_5$ is hydrogen, $C_1$–$C_{12}$alkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy or halogen;
$R_6$ and $R_{6a}$ are unsubstituted $C_1$–$C_{12}$alkyl, halogen-substituted $C_1$–$C_{12}$alkyl, phenyl-$C_1$–$C_6$alkyl, phenyl, where the radicals phenyl-$C_1$–$C_6$alkyl or phenyl are unsubstituted or are substituted 1–5 times by $C_1$–$C_6$alkyl, $C_1$–$C_{12}$alkoxy or halogen;
$R_7$, $R_{7a}$ and $R_8$ independently of one another are unsubstituted $C_1$–$C_{12}$alkyl, $C_1$–$C_{12}$alkoxy-substituted $C_1$–$C_{12}$alkyl, halogen-substituted $C_1$–$C_{12}$alkyl, OH-substituted $C_1$–$C_{12}$alkyl, $COOR_6$-substituted $C_1$–$C_{12}$alkyl, CN-substituted $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy or halogen, or $R_7$ and $R_8$, together with the N atom to which they are attached, form a 5- or 6-membered ring which optionally additionally contains O or S atoms;

$R_9$, $R_{10}$ and $R_{11}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or are substituted 1–5 times by $C_1$–$C_6$alkyl, $C_1$–$C_{12}$alkoxy or halogen;

$R_{12}$, $R_{13}$, $R_{14}$ and $R_{15}$ independently of one another are hydrogen, unsubstituted $C_1$–$C_{12}$alkyl, $C_1$–$C_{12}$alkoxy-substituted $C_1$–$C_{12}$alkyl, unsubstituted phenyl-$C_1$–$C_6$alkyl, mono- to penta-$C_1$–$C_6$alkyl-substituted phenyl-$C_1$–$C_6$alkyl, mono- to penta-$C_1$–$C_{12}$alkoxy-substituted phenyl-$C_1$–$C_6$alkyl, mono- to penta-halogen-substituted phenyl-$C_1$–$C_6$alkyl, unsubstituted phenyl, mono- to penta-$C_1$–$C_6$alkyl-substituted phenyl, mono- to penta-$C_1$–$C_{12}$alkoxy-substituted phenyl, mono- to penta-halogen-substituted phenyl, or the radicals $R_{12}$, $R_{13}$, $R_{14}$ and $R_{15}$ together form an aromatic ring to which further aromatic rings may be fused;

$R_{16}$, $R_{17}$, $R_{18}$, $R_{18a}$, $R_{19}$ and $R_{20}$ independently of one another are hydrogen, unsubstituted $C_1$–$C_{12}$alkyl, $C_1$–$C_{12}$alkoxy-substituted $C1$–$C_{12}$alkyl, OH-substituted $C_1$–$C_{12}$alkyl, halogen-substituted $C_1$–$C_{12}$alkyl, unsubstituted phenyl, $C_1$–$C_{12}$alkyl-substituted phenyl, $C_1$–$C_{12}$alkoxy-substituted phenyl, OH-substituted phenyl or halogen-substituted phenyl;

$R_{21}$, $R_{22}$ and $R_{23}$ independently of one another are $C_1$–$C_{12}$alkyl, $C_2$–$C_{12}$alkenyl or $C_3$–$C_{12}$cycloakyl, where the radicals $C_1$–$C_{12}$alkyl, $C_2$–$C_{12}$alkenyl and $C_3$–$C_{12}$cycloalkyl are unsubstituted or are substituted by $R_6OCO$ or CN, or $R_{21}$, $R_{22}$ and $R_{23}$ are unsubstituted phenyl-$C_1$–$C_6$alkyl, mono- to penta-$C_1$–$C_6$alkyl-substituted phenyl-$C_1$–$C_6$alkyl, mono- to penta-$C_1$–$C_{12}$alkoxy-substituted phenyl-$C_1$–$C_6$alkyl, mono- to penta-halogen-substituted phenyl-$C_1$–$C_6$alkyl, unsubstituted phenyl, mono- to penta-$C_1$–$C_6$alkyl-substituted phenyl, mono- to penta-$C_1$–$C_{12}$alkoxy-substituted phenyl or mono- to penta-halogen-substituted phenyl;

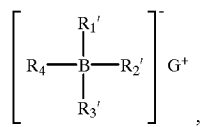
(Ia)

in which $R_1'$ and $R_2'$ independently of one another are phenyl which is substituted in at least one ortho-position to the bond to the boron atom by $C_1$–$C_{20}$alkyl, $C_2$–$C_{20}$alkyl which is interrupted by one or more radicals O, $S(O)_p$ or $NR_5$, or the phenyl radical is substituted in at least one ortho-position to the bond to the boron atom by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$, CN

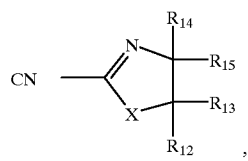

-continued

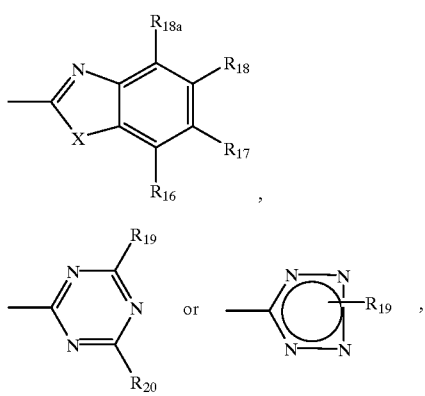

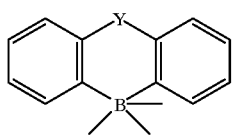

or the radicals $R_1'$ and $R_2'$ form bridges to produce structures of the formula II, IIa or IIb

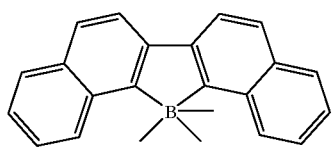
(II)

(IIa)

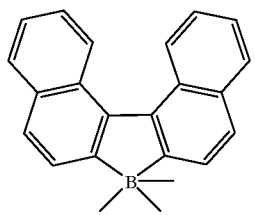
(IIb)

where the aromatic rings in the formula II are unsubstituted or are substituted by $C_1-C_{20}$alkyl, $C_2-C_{20}$alkyl which is interrupted by one or more radicals O, $S(O)_p$ or the aromatic rings are substituted by $NR_5$, $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, halogen, $R_9R_{10}P(O)_q$ or $R_9R_{10}R_{11}Sn$;

$R_3'$ is a bulky aromatic radical;

$R_4$ is phenyl, $C_1-C_{20}$alkyl, $C_2-C_{20}$alkyl interrupted by one or more radicals O, $S(O)_p$ or $NR_5$, or $R_4$ is $C_3-C_{12}$cycloalkyl, $C_2-C_8$alkenyl, phenyl-$C_1-C_6$alkyl or naphthyl-$C_1-C_3$alkyl, where the radicals $C_1-C_{20}$alkyl, $C_3-C_{12}$cycloalkyl, $C_2-C_8$alkenyl, phenyl-$C_1-C_6$alkyl or naphthyl-$C_1-C_3$alkyl are unsub stituted or are substituted by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$ halogen, $R_9R_{10}P(O)_q$, or CN;

Y is $(CH_2)_n$, CH=CH, C(O), $NR_5$, O, $S(O)_p$ or

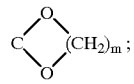

n is 0, 1 or 2;

m is 2 or 3;

p is 0, 1 or 2;

q is 0 or 1;

$R_5$ is hydrogen, $C_1-C_{12}$alkyl, phenyl-$C_1-C_6$alkyl or phenyl, where the radicals phenyl-$C_1-C_6$alkyl or phenyl are unsubstituted or substituted 1–5 times by $C_1-C_6$alkyl, $C_1-C_{12}$alkoxy or halogen;

$R_6$ and $R_{6a}$ independently of one another are $C_1-C_{12}$alkyl, phenyl-$C_1-C_6$alkyl or phenyl, where the radicals phenyl-$C_1-C_6$alkyl or phenyl are unsubstituted or substituted 1–5 times by $C_1-C_6$alkyl, $C_1-C_{12}$alkoxy or halogen;

$R_7$, $R_{7a}$ and $R_8$ independently of one another are $C_1-C_{12}$alkyl, $C_3-C_{12}$cycloalkyl, phenyl-$C_1-C_6$alkyl or phenyl, where the radicals phenyl-$C_1-C_6$alkyl or phenyl are unsubstituted or substituted 1–5 times by $C_1-C_6$alkyl, $C_1-C_{12}$alkoxy or halogen, or $R_7$ and $R_8$, together with the N atom to which they are attached, form a 5- or 6-membered ring which optionally additionally contains O or S atoms;

$R_9$, $R_{10}$ and $R_{11}$ independently of one another are $C_1-C_{12}$alkyl, $C_3-C_{12}$cycloalkyl, phenyl-$C_1-C_6$alkyl or phenyl, where the radicals phenyl-$C_1-C_6$alkyl or phenyl are unsubstituted or substituted 1–5 times by $C_1-C_6$alkyl, $C_1-C_{12}$alkoxy or halogen;

$R_{12}$, $R_{13}$, $R_{14}$ and $R_{15}$ independently of one another are hydrogen, unsubstituted $C_1-C_{12}$alkyl, $C_1-C_{12}$alkoxy-substituted $C_1-C_{12}$alkyl, unsubstituted phenyl-$C_1-C_6$alkyl, mono- to penta-$C_1-C_6$alkyl-substituted phenyl-$C_1-C_6$alkyl, mono- to penta-$C_1-C_{12}$alkoxy-substituted phenyl-$C_1-C_6$alkyl, mono- to penta-halogen-substituted phenyl-$C_1-C_6$alkyl, unsubstituted phenyl, mono- to penta-$C_1-C_6$alkyl-substituted phenyl, mono- to penta-$C_1-C_{12}$alkoxy-substituted phenyl or mono- to penta-halogen-substituted phenyl, or the radicals $R_{12}$, $R_{13}$, $R_{14}$ and $R_{15}$ together form an aromatic ring to which further aromatic rings may be fused;

X is N, S or O; and

G is a radical which is able for form positive ions as unimolecular photoinitiator and irradiating this mixture with light from the infrared range through the UV range to a wavelength of 200 nm.

2. The process according to claim 1 for producing pigmented and unpigmented coating materials, powder coatings, printing inks, painting plates, adhesives, dental compositions, waveguides, optical switches, colour proofing systems, glass fibre cable coatings, screen printing stencils, resist materials, for encapsulating electrical and electronic components, for producing composite compositions, for producing magnetic recording materials, for producing three-dimensional objects by means of stereolithography, for photographical reproductions, and as image recording material.

3. A coated substrate which is coated on at least one surface with a composition comprising a) at least one polymerizable ethylenically unsaturated compound and b) at least one compound of the formula I or I' according to claim 1 as unimolecular photoinitiator.

4. A process for the photographic production of relief images, which comprises subjecting a coated substrate according to claim 3 to imagewise exposure and then removing the unexposed areas with a solvent or exposing a coated substrate according to claim 3 by means of a movable laser beam (without mask) and then removing the unexposed areas with a solvent.

5. A process for the thermal polymerization of compounds containing ethylenically unsaturated double bonds, which comprises adding as polymerization initiator at least one compound of the formula I or I' according to claim 1.

6. A process for the photopolymerization of nonvolatile monomeric, oligomeric or polymeric compounds containing at least one ethylenically unsaturated double bond, which comprises adding to said compounds at least one compound of the formula I according to claim 1 as unimolecular photoinitiator and irradiating this mixture with light from the infrared range through the UV range to a wavelength of 200 nm.

7. A process according to claim 1 for producing holographic recordings.

8. A process for the thermal polymerization of compounds containing ethylenically unsaturated double bonds, which comprises adding as polymerization initiator at least one compound of the formula Ia or Ia'

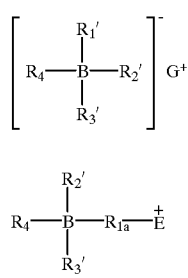

(Ia)

(Ia')

, in which $R_1'$ and $R_2'$ independently of one another are phenyl which is substituted in at least one ortho-position to the bond to the boron atom by $C_1$–$C_{20}$alkyl, $C_2$–$C_{20}$alkyl which is interrupted by one or more radicals O, $S(O)_p$ or $NR_5$, or the phenyl radical is substituted in at least one ortho-position to the bond to the boron atom by $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, $R_9R_{10}R_{11}Sn$, halogen, $R_9R_{10}P(O)_q$, CN

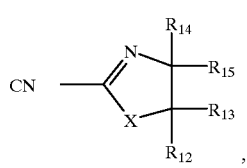

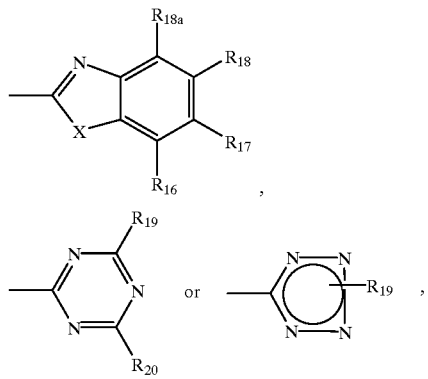

or the radicals $R_1'$ and $R_2'$ form bridges to produce structures of the formula II, IIa or IIb

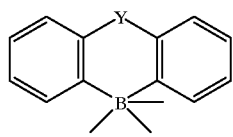
(II)

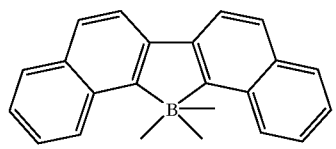
(IIa)

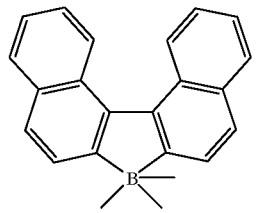
(IIb)

where the aromatic rings in the formula II are unsubstituted or are substituted by $C_1$–$C_{20}$alkyl, $C_2$–$C_{20}$alkyl which is interrupted by one or more radicals O, $S(O)_p$ or the aromatic rings are substituted by $NR_5$, $OR_6$, $R_6S(O)_p$, $R_6S(O)_2O$, $R_7R_8N$, $R_6OC(O)$, $R_7R_8NC(O)$, $R_9C(O)$, $R_9R_{10}R_{11}Si$, halogen, $R_9R_{10}P(O)_q$ or $R_9R_{10}R_{11}Sn$;

$R_{1a}'$ is a divalent aromatic hydrocarbon radical which is unsubstituted or is substituted by $C_1$–$C_6$alkyl, $OR_6$, $S(O)_pR_6$, $OS(O)_2R_6$, $NR_8R_7$, $C(O)OR_6$, $C(O)NR_8R_7$, $C(O)R_9$, $SiR_9R_{10}R_{11}$ or halogen, or $R_{1a}'$ is phenyl-$C_1$–$C_6$alkylene;

$R_3'$ is a bulky aromatic radical, $R_4$ is phenyl, $C_1$–$C_{20}$alkyl, $C_2$–$C_{20}$alkyl interrupted by one or more radicals O, $S(O)_p$ or $NR_5$, or $R_4$ is $C_3$–$C_{12}$cycloalkyl, $C_2$–$C_8$alkenyl, phenyl-$C_1$–$C_6$alkyl or naphthyl-$C_1$–$C_3$alkyl, where the radicals $C_1$–$C_{20}$alkyl, $C_3$–$C_{12}$cycloalkyl, $C_2$–$C_8$alkenyl, phenyl-$C_1$–$C_6$alkyl or naphthyl-$C_1$–$C_3$alkyl are unsub stituted or are substituted by $OR_6$, $R_6S(O)_p$, $R_6S(O)_2O$, $R_7R_8N$, $R_6OC(O)$, $R_7R_8N(O)$, $R_9C(O)$, $R_9R_{10}R_{11}Si$, $R_9R_{10}R_{11}Sn$, halogen, $R_9R_{10}P(O)_q$, or CN;

Y is $(CH_2)_n$, CH=CH, C(O), $NR_5$, O, $S(O)_p$ or

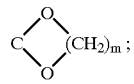

n is 0, 1 or 2;
m is 2 or 3;
p is 0, 1 or 2;
q is 0 or 1;
E is $R_{21}R_{22}R_{23}P$, $R_7R_{7a}R_8N$ or $R_6R_{6a}S$;
$R_5$ is hydrogen, $C_1$–$C_{12}$alkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy or halogen;
$R_6$ and $R_{6a}$ independently of one another are $C_1$–$C_{12}$alkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy or halogen;
$R_7$, $R_{7a}$ and $R_8$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy or halogen, or $R_7$ and $R_8$, together with the N atom to which they are attached, form a 5- or 6-membered ring which optionally additionally contains O or S atoms;
$R_9$, $R_{10}$ and $R_{11}$ independently of one another are $C_1$–$C_{12}$alkyl, $C_3$–$C_{12}$cycloalkyl, phenyl-$C_1$–$C_6$alkyl or phenyl, where the radicals phenyl-$C_1$–$C_6$alkyl or phenyl are unsubstituted or substituted 1–5 times by $C_1$–$C_6$alkyl, $C_1$–$C_{12}$alkoxy or halogen;

$R_{12}$, $R_{13}$, $R_{14}$ and $R_{15}$ independently of one another are hydrogen, unsubstituted $C_1$–$C_{12}$alkyl, $C_1$–$C_{12}$alkoxy-substituted $C_1$–$C_{12}$alkyl, unsubstituted phenyl-$C_1$–$C_6$alkyl, mono- to penta-$C_1$–$C_6$alkyl-substituted phenyl-$C_1$–$C_6$alkyl, mono- to penta-$C_1$–$C_{12}$alkoxy-substituted phenyl-$C_1$–$C_6$alkyl, mono- to penta-halogen-substituted phenyl-$C_1$–$C_6$alkyl, unsubstituted phenyl, mono- to penta-$C_1$–$C_6$alkyl-substituted phenyl, mono- to penta-$C_1$–$C_{12}$alkoxy-substituted phenyl or mono- to penta-halogen-substituted phenyl, or the radicals $R_{12}$, $R_{13}$, $R_{14}$ and $R_{15}$ together form an aromatic ring to which further aromatic rings may be fused;

$R_{21}$, $R_{22}$ and $R_{23}$ independently of one another are $C_1$–$C_{12}$alkyl, $C_2$–$C_{12}$alkenyl or $C_3$–$C_{12}$cycloalkyl, where the radicals $C_1$–$C_{12}$alkyl, $C_2$–$C_{12}$alkenyl and $C_3$–$C_{12}$cycloalkyl are unsubstituted or are substituted by $R_6OCO$ or CN, or $R_{21}$, $R_{22}$ and $R_{23}$ are unsubstituted phenyl-$C_1$–$C_6$alkyl, mono- to penta-$C_1$–$C_6$alkyl-substituted phenyl-$C_1$–$C_6$alkyl, mono- to penta-$C_1$–$C_{12}$alkoxy-substituted phenyl-$C_1$–$C_6$alkyl, mono- to penta-halogen-substituted phenyl-$C1$-$C_6$alkyl, unsubstituted phenyl, mono- to penta-$C_1$–$C_6$alkyl-substituted phenyl, mono- to penta-$C1$-$C1_2$alkoxy-substituted phenyl or mono- to penta-halogen-substituted phenyl;

X is N, S or O; and

G is a radical which is able to form positive ions.

* * * * *